US009809557B2

(12) United States Patent
Larsen et al.

(10) Patent No.: US 9,809,557 B2
(45) Date of Patent: *Nov. 7, 2017

(54) PRODRUGS OF NON-STEROID ANTI-INFLAMMATORY AGENTS (NSAIDS)

(71) Applicant: Claus Selch Larsen, Lejre (DK)

(72) Inventors: Claus Selch Larsen, Lejre (DK); Susan Weng Larsen, Rødvore (DK); Mette Agergaard Thing, Copenhagen (DK); Jesper Langgaard Kristensen, Copenhagen (DK); Henrik Jensen, Roskilde (DK); Jesper Østergaard, Farum (DK)

(*) Notice: Subject to any disclaimer, the term of this patent is extended or adjusted under 35 U.S.C. 154(b) by 0 days.

This patent is subject to a terminal disclaimer.

(21) Appl. No.: 14/355,010

(22) PCT Filed: Oct. 31, 2012

(86) PCT No.: PCT/DK2012/050400
§ 371 (c)(1),
(2) Date: Apr. 29, 2014

(87) PCT Pub. No.: WO2013/064153
PCT Pub. Date: May 10, 2013

(65) Prior Publication Data
US 2014/0315960 A1    Oct. 23, 2014

(30) Foreign Application Priority Data

Oct. 31, 2011  (DK) .................... 2011 70591

(51) Int. Cl.
| | | |
|---|---|---|
| *A61K 31/44* | (2006.01) |
| *C07D 235/06* | (2006.01) |
| *A61K 47/48* | (2006.01) |
| *C07C 219/10* | (2006.01) |
| *C07C 219/32* | (2006.01) |
| *C07C 229/42* | (2006.01) |
| *C07D 487/04* | (2006.01) |
| *C07D 233/61* | (2006.01) |
| *C07D 235/16* | (2006.01) |
| *C07D 235/18* | (2006.01) |
| *C07D 213/55* | (2006.01) |

(52) U.S. Cl.
CPC ...... *C07D 235/06* (2013.01); *A61K 47/48023* (2013.01); *A61K 47/48061* (2013.01); *C07C 219/10* (2013.01); *C07C 219/32* (2013.01); *C07C 229/42* (2013.01); *C07D 213/55* (2013.01); *C07D 233/61* (2013.01); *C07D 235/16* (2013.01); *C07D 235/18* (2013.01); *C07D 487/04* (2013.01)

(58) Field of Classification Search
CPC .. C07D 235/06; C07D 235/18; C07D 233/61; C07D 213/16; C07D 487/04; C07D 235/16; C07D 213/55; C07C 229/42; C07C 219/10; C07C 219/32; C07C 219/31; A61K 47/48061; A61K 47/48023

USPC ....... 514/357, 539, 399, 394, 510, 277, 413, 514/534; 546/335, 342; 548/341.5, 548/310.1, 516; 560/56, 106, 43

See application file for complete search history.

(56) References Cited

U.S. PATENT DOCUMENTS 3,973,024 A    8/1976   Haas et al.

FOREIGN PATENT DOCUMENTS

| EP | 0 124 186 A2 | 11/1984 | |
|---|---|---|---|
| FR | 2 336 126 A1 | 7/1977 | |
| GB | 927 119 A | 5/1963 | |
| WO | WO 2005/046575 A2 | 5/2005 | |
| WO | WO2008012602 A1 * | 1/2008 | |
| WO | WO 2008012602 A1 * | 1/2008 | ........... C07C 229/42 |

OTHER PUBLICATIONS

RN1615-14-1(available Nov. 16, 1984, corresponding to instantly claimed 2-(1H-imidazol-1-yl)ethan-1-ol).*
Semalty et al (Acta Pharm., 2009, 59, 335-344).*
Majumdar (Tet. Lett., 2007, 48, 4609-4611).*
Mork et al., "Stereoselective enzymatic hydrolysis of various ester prodrugs of ibuprofen and flurbiprofen in human plasma," Pharmaceutical Research, vol. 9, No. 4, pp. 492-496, Jan. 1, 1992.
Parmeshwari et al., "Synthesis and Evaluation of Some Gastrointestinal Sparing Anti-Inflammatory Aminoethyl Ester Derivatives of Naphthalene-Based NSAID's," Archiv Der Pharmazie, vol. 340, No. 2, pp. 88-94, Feb. 1, 2007.
Haricharan et al., "A Green Chemistry Approach to Ibuprofen Piconol," Synthetic Communications, vol. 35, No. 2, pp. 209-212, Jan. 1, 2005.

(Continued)

*Primary Examiner* — Jeffrey S Lundgren
*Assistant Examiner* — Ibrahim D Bori
(74) *Attorney, Agent, or Firm* — F. Aaron Dubberley

(57) ABSTRACT

The present invention relates to novel depot formulations (prodrugs) comprising an immobility promoting unit linked via an ester to an active pharmaceutical ingredient, i.a. common NSAIDs. The novel depot formulations are suitable for intra-articular injections and are soluble at slightly acidic pH to facilitate ease of injection, and sparingly soluble at physiological pH thereby precipitating at the site of administration. The precipitate will slowly dissolve and the active drug is released from dissolved depot formulation following esterase mediated cleavage of the ester link between the immobility promoting unit and the active pharmaceutical agent.

20 Claims, 5 Drawing Sheets

(56) References Cited

OTHER PUBLICATIONS

Rademann et al., "Alkylating Polymers: Resin-Released Carbenium Ions as Versatile Reactive Intermediates in Polymer-Assisted Solution-Phase Synthesis," Angewandte Chemie, vol. 40, No. 2, pp. 381-385, Jan. 19, 2001.
Majumdar et al., "alpha-(1H-Imidazol-1-yl)alkyl (IMIDA) carboxylic acid esters as prodrugs of carboxylic acid containing drugs," Tetrahedron Letters, vol. 48, No. 26, pp. 4609-4611, Jun. 25, 2007.
Silviu et al., "Non-narcotic adjuvants may improve the duration and quality of analgesia after knee arthroscopy: a brief review," Canadian Journal of Anesthesia, vol. 51, No. 10, pp. 975-978, Dec. 1, 2004.
Pschorr, "Halogenderivate von Morphin und Codeïn und deren Abbau," Berichte der Deutschen Chemischen Gesellschaft, vol. 39, No. 3, pp. 3130-3139, 1906.
International Search Report issued in application No. PCT/DK2012/050400 dated Jan. 25, 2013.
International Type Search Report issued in application No. DK 201170591 dated Apr. 24, 2012.

* cited by examiner

Figure 1: The structures of the twenty five prodrugs with the NSAIDs ketorolac, diclofenac, ibuprofen, and naproxen attached to different immobility promoting units (IPUs) – continues on next page..
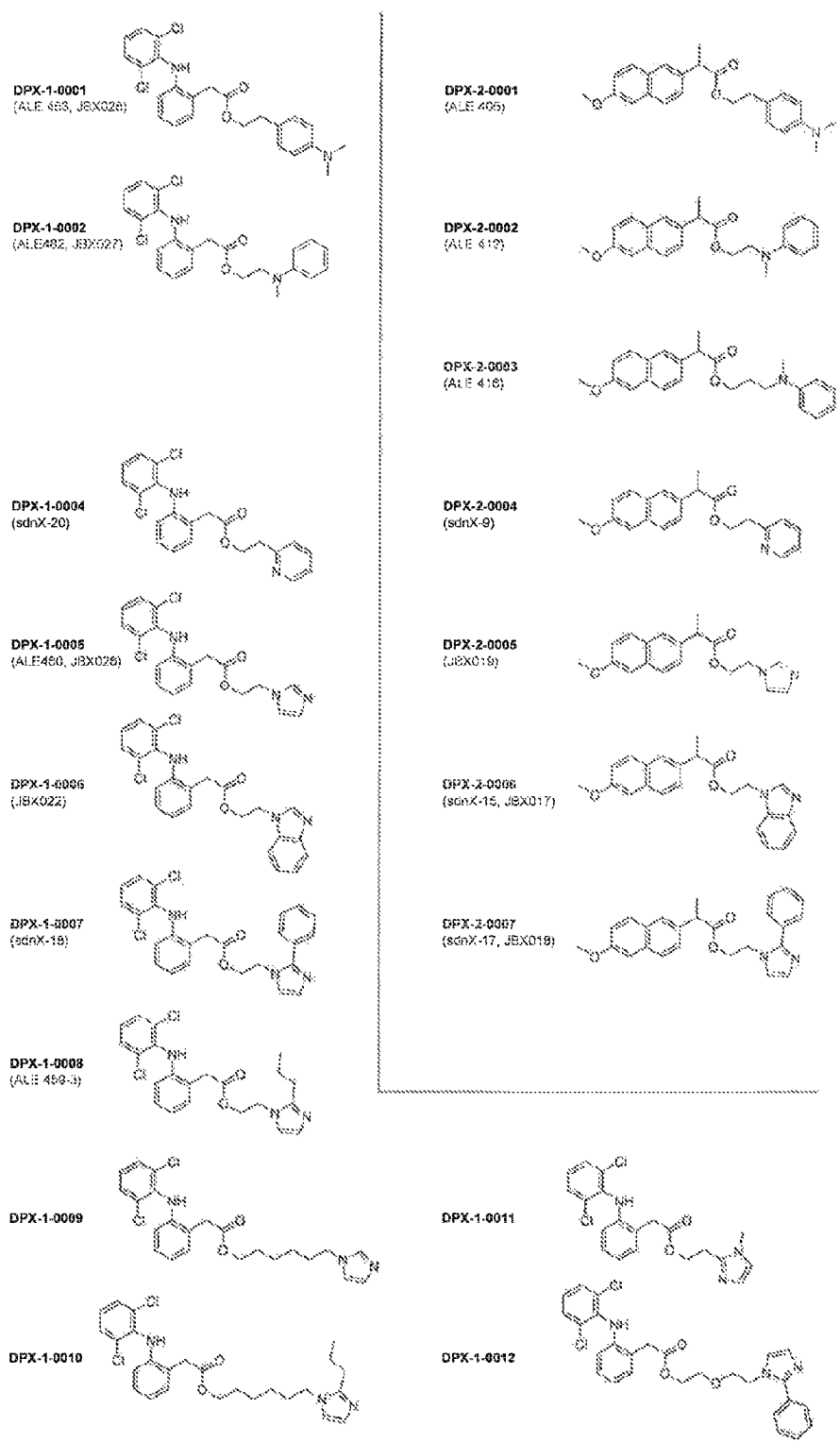

Figure 2. Time course for DPX-4-0001 (ALE 408) and ketorolac in solution after addition of solid DPX-4-0001 (ALE 408) to synovial fluid at 37°C illustrating the cleavage of dissolved prodrug to the active substance.
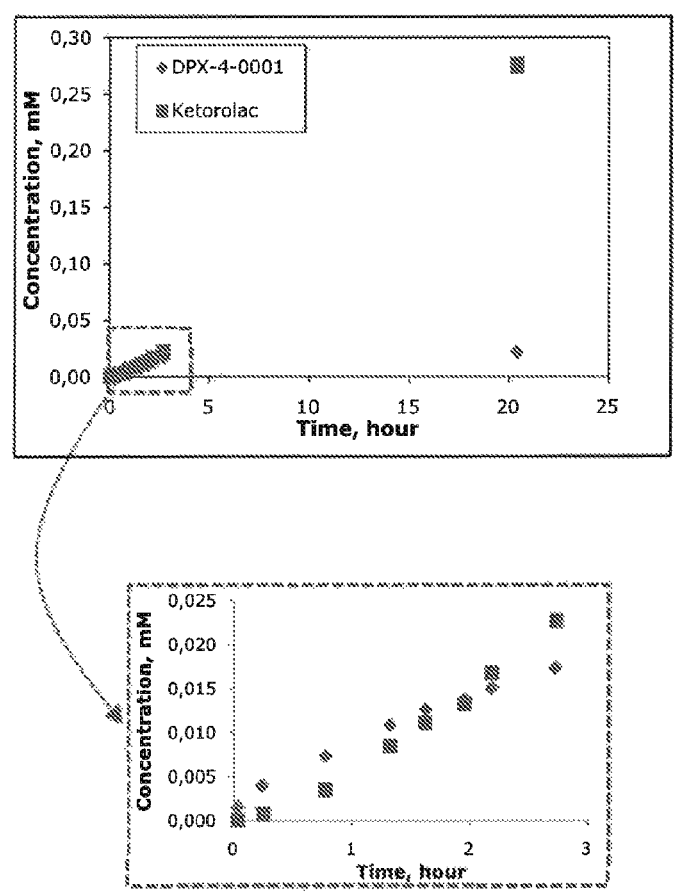

Figure 3 – Precipitation of DPX-4-0001 after addition of a concentrated aqueous acidic solution to buffer pH 7.4 solution followed by non-enzymatic hydrolysis of dissolved DPX-4-0001 to ketorolac.
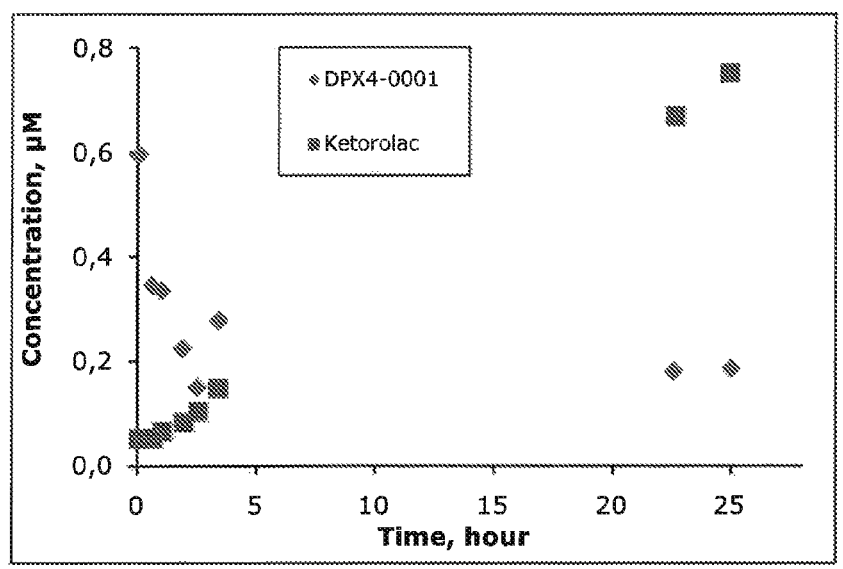

Figure 4: Factors influencing the pharmacokinetic fate of the prodrug/drug after administration of the prodrug into the joint. The prodrug dissolved is converted into the active drug by enzymatic cleavage of the prodrug bond.
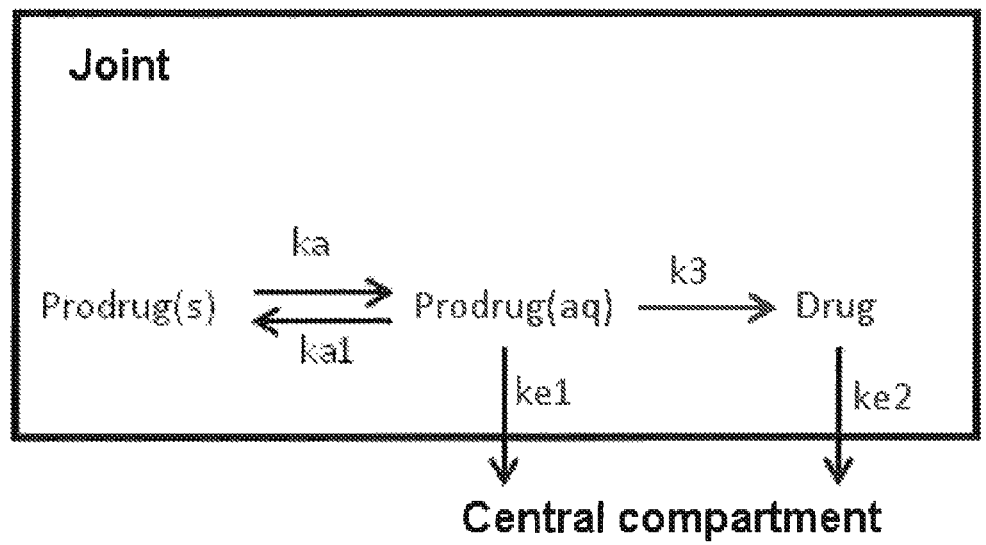

PRODRUGS OF NON-STEROID ANTI-INFLAMMATORY AGENTS (NSAIDS)

FIELD OF THE INVENTION

The present invention relates to novel prodrugs of NSAIDs comprising an immobility promoting unit covalently linked, in the form of an ester bond, to an active pharmaceutical ingredient, i.a. common NSAIDs. The novel compounds are soluble at acidic pH but precipitate at neutral/slightly alkaline pH. Thus, the compounds can be formulated as slightly acidic solutions, but upon injection into a joint the prodrug will precipitate and act as a depot of the drug. In the joint, the prodrug will slowly dissolve and be converted to the active drug substance by hydrolytic enzymes present in the joint. The invention furthermore relates to pharmaceutical compositions of the novel prodrugs, as well as the use of the compounds and compositions as medicaments, and for use in specific treatments of i.a. injured and inflamed joints.

BACKGROUND OF THE INVENTION

Modern postoperative pain control focuses on early mobilization and rapid discharge of patients following surgery. Although minimally invasive of nature, arthroscopic procedures do produce pain and inflammation. As a result patients may be prevented from returning to work for weeks after surgery.

Findings have shown that aggressive pain management, including local intra-articular drug therapy, in the early postoperative period can improve convalescence after surgery significantly.

Over the years the efficacy of a significant number of drugs and drug combinations to provide pain relief after intra-articular injection has been investigated. Efficacious intra-articular monotherapeutic approaches include (i) NSAIDs, (ii) local anaesthetics, and (iii) opiates (e.g. morphine). Following arthroscopic procedures promising pain alleviating effects of different intra-articular multimodal analgesic regimens have been reported. Most combinations used consisted of 2-3 drugs selected from opiates, local anaesthetics and anti-inflammatory agents (NSAIDs or corticosteroids) (ref. 1, 2).

Looking to future intra-articular multimodal therapies, particular attention needs to be paid to tailor the duration of action of the individual therapeutic agents whilst keeping the dose of administered compounds to a minimum.

Treatment of e.g. inflammation with NSAIDs is difficult to attain in a site-specific manner. Consequently, a systemic approach is usually employed, where an oral dose is spread through-out the body, thereby limiting the effective dose at the injured or inflamed site, and increasing the emergence of side effects due to high concentrations of NSAIDs in other areas of the body. Attempts to inject the NSAID locally at the site of treatment will only be effective for a few hours, by which time the water-soluble injected drug will, for practical purposes, have diffused out of the joint space, and into the general circulation. This short half-life of intra-articular disappearance of NSAIDs and other small-molecule drugs, which have a high water solubility at and around physiological pH, is inhibitive for a continuous release/depot effect.

Simple depot suspensions may be thought to be a preferred way to deliver an immobilised drug since a high drug load can be achieved and minimal pharmaceutical excipients are needed. However, in spite of the relative simplicity of this formulation type compared to more advanced and complex controlled release drug delivery systems, the formulation of (physically) stable injectable suspensions with good shelf-life poses considerable manufacturing challenges.

The problem of administering depot formulations to joints has previously been attempted to be solved by injecting for example suspensions made from steroid esters. Various long-acting steroid ester formulations (aqueous microcrystalline suspensions) are marketed for intra-articular injection. The duration of action of such injectables are 2-6 weeks and thus not indicated for postoperative pain control following minor arthroscopic surgery, which is typically 1-7 days. The drawbacks of using a microcrystalline suspension include that suspensions are difficult to sterilize (e.g. sterilization by filtration is excluded) and that the particle size distribution of the suspended particles may change over time, thereby also changing the in vivo drug release profile. Thus, the formulation of (physically) stable injectable suspensions with good shelf-life poses considerable manufacturing challenges.

Alternatives to microcrystalline depot formulations as described above are injecting a poorly water-soluble salt of the drug solubilised in a co-solvent, which is then precipitated in situ at the injected site (upon contact with water/the biologic fluid, in which the salt is poorly soluble). The drawbacks of this approach is that the release profile is difficult to control—either the release is too fast (1-2 hours) or too slow.

Hydrogels have also been employed, as a possible depot formulation principle. One of the drawbacks of hydrogels is that some do leave behind insoluble residual material in the joint, which is undesirable. Further, a hydrogel does not enable simultaneous release of analgesics (local anaesthetics or opiates over a 24 h period) and anti-inflammatory agents (NSAIDs or corticosteroids over about 7 days), which has been found to improve convalescence after surgery significantly.

There is thus a need in the art for intra-articular depot formulations that may be tailored to have a release profile over 1-7 days.

Further, there is a need for a formulation that does not leave behind insoluble residual material in the joint.

Further, there is a need for a formulation that allows the tailoring of different release profiles in a multimodal regimen.

DESCRIPTION OF THE INVENTION

The present invention was made in view of the prior art described above, and the object of the present invention is to provide novel prodrugs of NSAIDs which can be formulated to allow the administered drug to be released over e.g. 1-7 days whilst keeping the dose of administered compounds to a minimum.

In describing the embodiments of the invention specific terminology will be resorted to for the sake of clarity. However, the invention is not intended to be limited to the specific terms so selected, and it is understood that each specific term includes all technical equivalents which operate in a similar manner to accomplish a similar purpose.

In general, small-molecule solutes (including NSAIDs) are rapidly cleared from the synovial space after intra-articular (IA) injection. The present invention provides prodrug compounds that form precipitates of low solubility when they are injected into the joint cavity, effectively immobilising the prodrug at the site of required action. The precipitates are in equilibrium with a low concentration of dissolved prodrug (see FIG. 4). The parent drug is regenerated from dissolved prodrug following esterase/hydrolase-mediated cleavage of the prodrug ester bond in the injured or inflamed joint cavity, so releasing the active dissolved drug. Due to the slow dissolution process, therapeutic drug concentrations can be maintained in the joint cavity over relevant and extended periods of time mainly dictated by the free fraction concentration of the prodrug in the inflamed synovial fluid. The prodrug derivatives are designed to have a high solubility in slightly acidic solution but this solubility decreases substantially with increasing pH (up to around physiological pH (about pH 7.4)); the prodrugs are obtained by covalent attachment of water-soluble drug compounds to appropriate IPUs (immobility-promoting units, such as weak bases containing an amino/amine functional group with a pKa value in the range of about 4 to about 7.4). Thus, injection of prodrug in the form of slightly acidic aqueous solutions into the joint leads to prodrug precipitation in synovial fluid (in situ precipitate formation). Subsequent availability of the active species is dictated by the rate of dissolution of the precipitate and cleavage of dissolved prodrug by action of hydrolases, including esterases present in the synovial fluid of injured and/or inflamed joints.

Depot drugs of the present invention, which are also referred to as prodrugs, may be useful for monotherapies as well as in multimodal analgesia regimens. The duration of action of the administered medicine will be (roughly) inversely proportional to the rate of dissolution of the precipitated prodrug in the synovial fluid; the rate of dissolution is proportional to the solubility of the prodrug, and this latter parameter can be modified by using IPU's having different physicochemical properties—it is therefore possible to match different IPUs to any particular drug compound (capable of e.g. esterification to the IPUs) in order to achieve a variety of desired release profiles.

To solve the problem the present invention provides a compound of formula (I):

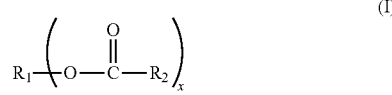

(I)

wherein $R_1$ represents an immobility promoting unit selected from an organic moiety with a molecular weight lower than 1500 g/mol such as lower than 1000 g/mol comprising one or more nitrogen containing moieties each with a $pK_a$ of between 4 and 7.6 at 37° C.; —O—(C=O)—$R_2$ represents an acyloxy residue of a carboxylic acid group contained within a non-steroidal anti-inflammatory agent (NSAID); x is an integer selected from 1, 2, 3 or 4; and pharmaceutically acceptable salts, solvates and hydrates thereof, and salts formed with the same or different NSAID than the NSAID represented by —O—(C=O)—$R_2$.

$R_1$ is an immobility promoting unit, which can have one or more hydroxyl functional groups, which can be used to attach an active pharmaceutical ingredient in the form of an ester bond. The function of the IPU is to immobilise the prodrug of formula (I) so that it precipitates when injected into an area containing a bodily fluid at and around physiological pH, but also such that the prodrug of formula (I) is soluble at slightly acidic pH, such as pH 1.5 to 5 for example between pH 2 and 4, such as pH 3 to 4, for example 3.3, 3.5, 3.7.

By modifying the $R_1$ moiety by selecting one or more nitrogen containing moieties, the prodrug of formula (I) can be tailored to precipitate at physiological pH, and be soluble at a pH that is between 2 to 6 units lower, as explained above.

The prodrug of formula (I) is a small molecule drug, which is a low molecular weight organic compound that is not a polymer. By low molecular weight organic compound is considered a compound that has a molecular weight below 1500 g/mol, such as below 1000 g/mol.

Nitrogen containing moieties are well-known to the skilled person, and can encompass any structure that contain a nitrogen atom, and which has a $pK_a$ value of between 4 and 7.6. Suitable nitrogen containing moieties may be selected from substituted or unsubstituted phenylamino, imidazolyl, isoquinolinyl, quinolinyl, benzimidazolyl, acridinyl, pyridinyl,

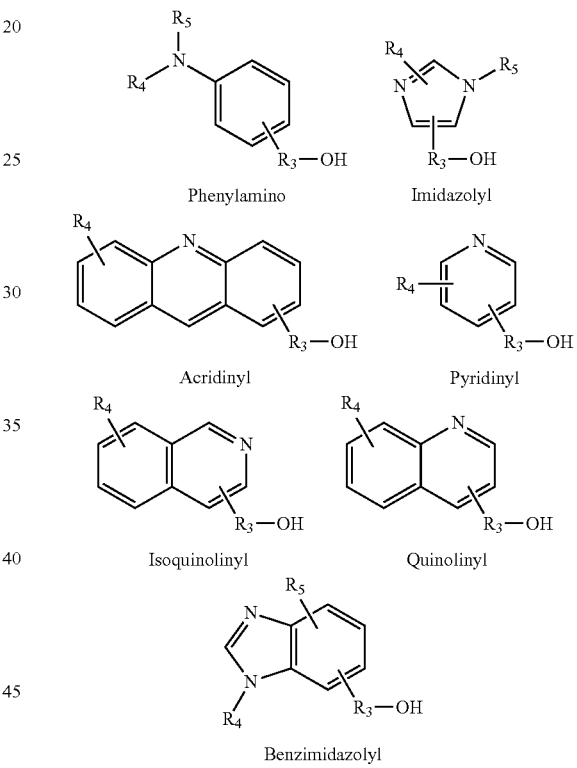

The OH-group (primary, secondary or tertiary alcohol group) of the IPU is attached to the core of the IPU through a so-called linker $R_3$ (where $R_3$ is alkyl, or alkoxyalkyl). $R_3$, which is situated between the IPU core and the NSAID, can be attached at any point on the IPU core, either on a ring carbon- or nitrogen atom. If $R_3$ is attached to one of the IPU ring carbon atoms, the linker chain may be composed of from one to eight atoms. In most cases linker chains comprising at least two carbon atoms are preferred unless the deliberated purpose has been to alter the $pK_a$ of a IPU ring nitrogen atom.

In case the linker chain is attached to a nitrogen atom, the linker may be composed of from two to eight carbon atoms. In the latter case use of a simple methylene group linker leads to the formation of undesirable aminal structures having poor chemical stability in an aqueous environment.

Also two or more $R_3$—OH-groups may be attached to the IPU core. The IPU core might also contain additional substituents as indicated by $R_4$ and $R_5$ (where $R_4$ and $R_5$ are hydrogen, alkyl, alkoxyalkyl, or phenyl). The substituents $R_4$ and $R_5$ may also contain functional groups (such as, e.g. an ether group) or atoms (such as, e.g. oxygen) in order to optimize the hydrophilic-lipophilic balance of the individual prodrug derivative. The positions of the 3 (possibly more) substituents are interchangeable. In the present context, the term "alkyl" designates $C_{1-8}$ alkyl which may be straight or branched, such as methyl, ethyl, propyl, isopropyl, butyl, pentyl, hexyl, heptyl, or octyl. Alkoxyalkyl designates alkoxy groups (e.g. methoxy, ethoxy, and propoxy) attached to an alkyl group as defined above.

The one or more nitrogen containing moieties of the novel prodrugs must each have a $pK_a$ of between 4 and 7.6 at 37° C. This requirement is important in order to ensure a higher water-solubility at an acidic/slightly acidic pH than at neutral/slightly alkaline pH. To this end, the present inventors have exploited the general knowledge that a certain distance between the N atom and the —O—(C=O)—$R_2$ can be used to avoid an unwanted effect on the $pK_a$ of the amino group. Thus, when e.g. imidazole or substituted imidazole is the nitrogen containing moiety, the N atom and the —O—(C=O)—$R_2$ should be separated by a carbon chain containing two or more carbon atoms. It is contemplated that this also applies to the other nitrogen containing compounds mentioned.

As mentioned above, the IPU part ($R_1$) of the prodrug of formula (I) comprises one or more nitrogen containing moieties. Nitrogen containing moieties are well-known to the skilled person, and can encompass any structure that contain a nitrogen atom, and which has a $pK_a$ value of between 4 and 7.6. Suitable nitrogen containing moieties may be selected from phenylamino, imidazolyl, isoquinolinyl, quinolinyl, benzimidazolyl, acridinyl, pyridinyl, which all are well suited because they may be tailored by substitution to have a $pK_a$ value of between 4 and 7.6. This may be done by proper manipulation of the moiety by substitution with electron donating groups and/or electron withdrawing groups. Thus, electron donating substituents as alkoxy, phenoxy, amine, alkyl will increase the pKa of the IPU. Consequently, electron withdrawing substituent as aldehydes, ketones, esters, amides, nitrogroups, halogens will lower the pKa. For instance aniline may be substituted with the electrondonating groups such as —OH, $CH_3O$—, $CH_3CH_2O$— and $CH_3$— in para position to increase the pKa of aniline from 4.6 to around 5.2 to 5.5. $pK_a$ of anilines may additionally be manipulated by N-substitution, as well as combinations. It is well-known to the person skilled in the art to manipulate nitrogen moieties such as for example anilines in this manner to tune the $pK_a$. See for instance the document "*pKa Data Compiled by R. Williams*" (Ref. 3), which can be downloaded from the internet (http://research.chem.psu.edu/brpgroup/pKa_compilation.pdf), and which is the same document that has been cited in the following reference: Caballero et al. (2006) "Theoretical prediction of relative and absolute pKa values of aminopyridines", Biophysical Chemistry 124(2), p 155-160 (Ref. 4).

More specifically, and as it appears from the examples herein illustrated by compounds DPX-1-0005 to DPX-1-0012 (which are all imidazole derivatives) it is possible to vary:
1) the point of attachment on the Imidazole (see e.g. above)
2) adjust the pKa by varying the substituents on the imidazole (cf above)
3) adjust the solubility of the prodrug by varying the substituents on the imidazole;

Increasing the lipophillicity of the IPU will reduce the aqueous solubility of IPU and thus the entire produg. If the IPU is substituted with a hydrophilic substituent, the solubility of the IPU and thus the prodrug will increase. Such substituents could be amines, alchohols, acids, ethers. The nature and length of the linker between the IPU and the NSAID can be used to modify the solubility of the produg. Straight chain aliphatic linkers will reduce the solubility of the prodrug the longer they get. Substitution the linker for a hydrophilic linker like polyethylene glycol will increase the solubility of the entire prodrug.
4) The nature and length of the linker between the IPU and the NSAID can also be used to enable spatial separation between the IPU and the drug to allow the hydrolytic enzyme access to the prodrug bond (minimize steric hindrance);
5) how it is possible to combine the permutations independently of each other.

Although this is illustrated for imidazole as IPU the same adjustments may be made to the other IPU mentioned herein.

The inventors of the present invention found that a nitrogen-containing immobility promoting unit (IPU) covalently attached to an active pharmaceutical ingredient in the form of an ester bond can be tailored to be soluble in slightly acidic environments (making it easy to formulate and sterilise as well as to inject), and sparingly soluble in a pH range close to physiological pH of about pH 7.4, thereby providing a depot of a drug substance, which depot (prodrug) by actions of enzymes residing in the pathological site (e.g. esterases or hydrolytic enzymes in tissues of the joint cavity including the synovial fluid) can release the NSAID in the joint space.

Thus, the present invention offers tailored release of active pharmaceutical ingredients—applicable to monotherapy as well as multimodal regimens—and the possibility to tailor their concomitant release.

In some embodiments of the compounds of present invention, x is 1, 2, 3, or 4.

In some embodiments of the compounds of present invention x is 1 or 2, notably 1.

In general, the prodrugs of the present invention may have a solubility as low as 0.05 µg/ml in 10 mM or 67 mM PBS (phosphate buffer solution) at 37° C. and pH 7.4. Based on solubilities determined at pH 7.4, solubilities of prodrugs at pH 3 as high as 100 mg/ml have been estimated. The increase in solubility is theoretically a factor 1000, when the pH is decreased with 3 pH units below the $pK_a$ value of the pro-moiety. However, there may be deviations therefrom.

The acyloxy residue (—O—(C=O)—$R_2$) is selected from the corresponding carboxylic acid group containing API's belonging to the class of non-steroidal anti-inflammatory agents (NSAIDs).

The NSAIDs are selected from the list consisting of: naproxen, ibuprofen, ketorolac, ketoprofen, fenoprofen, flurbiprofen, oxaprofen, diclofenac, tolmetin, tolfenamic acid, mefenamic acid, sulindac, indomethacin, salicylic acid, acetylsalicylic acid, deflunisal, loxoprofen, indoprofen, priprofen, clidanac, fenclorac, meclofenamate, benoxaprofen, carprofen, isofezolac, aceclofenac, fenbufen, etodolic acid, fleclozic acid, amfenac, efenamic adic, bromfenac, flenclofenac, alcofenac, orpanoxin, zomopirac, flufenamic acid, niflumic acid, pranoprofen, zaltoprofen, and suprofen. Preferred NSAIDs are diclofenac, naproxen and ibuprofen since these drug substances are the most potent and prescribed NSAIDs.

The prodrug of formula (I) may be polyvalent, meaning that x is selected such that it x is in the range of from 1 to 4, such as 1, 2, 3, 4. For example the prodrug of formula (I) may be monovalent, meaning that x equals 1, divalent meaning that x =2), trivalent (x=3), tetravalent (x=4). In preferred embodiments, the prodrug of formula (I) is monovalent, or divalent, preferably with x being 1.

The prodrug of formula (I) may be formulated as a pharmaceutically acceptable salt, or as a solvate or hydrate thereof. By pharmaceutically acceptable salts means those salts of compounds of the invention that are safe and effective for injection in mammals, in particular intra-articular injection, and that possess the desired biological activity. Pharmaceutically acceptable salts include salts of basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, oxalate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate salts. Suitable salts are also those formed with the same NSAID as the one included in the prodrug, i.e. if the produg is IPU-diclofenac, then a suitable salt is the diclofenac salt of IPU-didofenac. Suitable salts are also those formed from another NSAID than the one included in the prodrug, i.e. if the prodrug is IPU-diclofenac, then a suitable salt is e.g. the naproxen salt of the IPU-diclofenac prodrug.

In some embodiments of the compounds of present invention, $R_1$ is selected from the list consisting of the $R_1$ moieties of the $R_1$—OH compounds below.

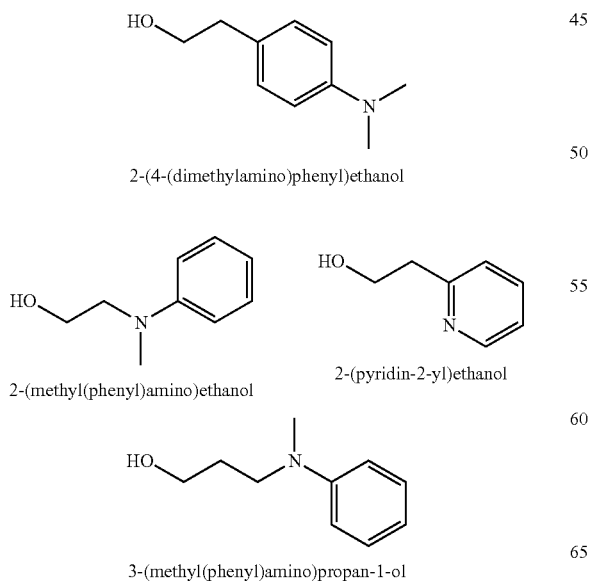

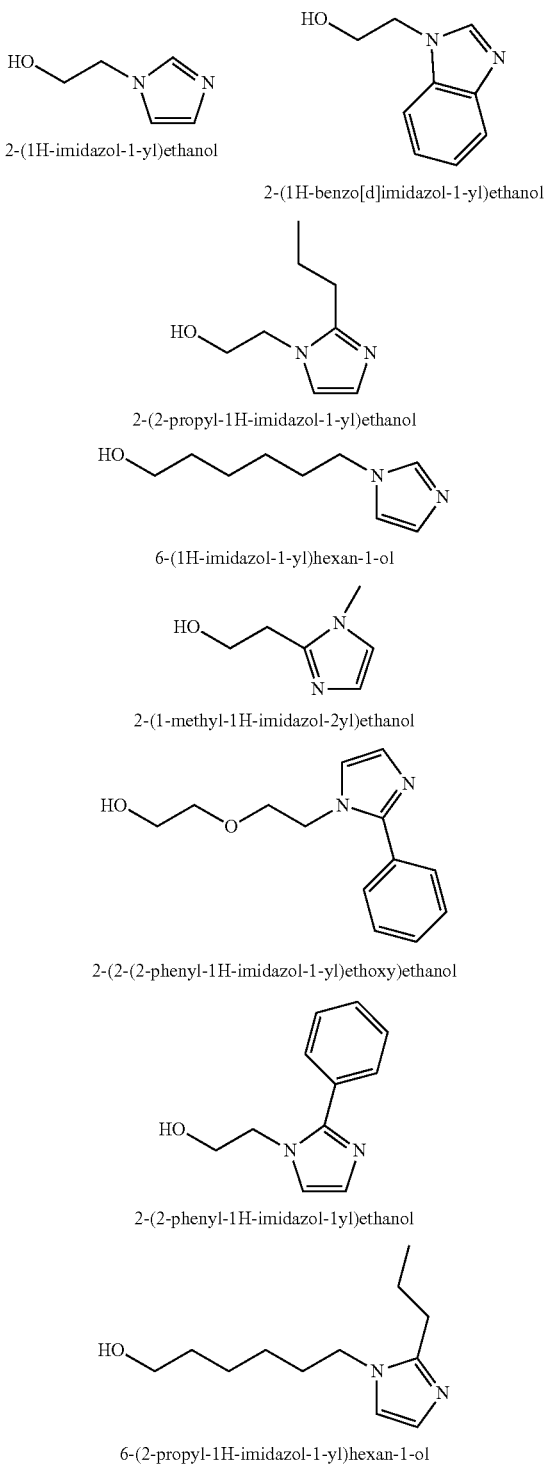

The above-mentioned IPUs may all be linked to any of the NSAIDs mentioned herein and the resulting structures are all encompassed by the present invention.

Specific examples of compounds of the present invention are given in the following. The invention is not limited thereto, the structures are given by way of example.

Example of prod rugs of the invention, where the NSAID is diclofenac:

DPX-1-0001

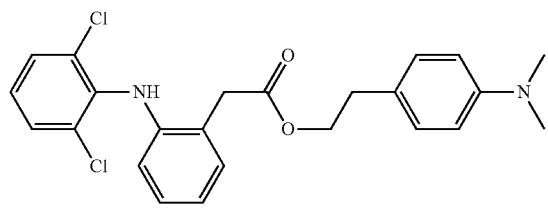

4-(dimethylamino)phenethyl
2-(2-((2,6-dichlorophenyl)amino)phenyl)acetate

DPX-1-0002

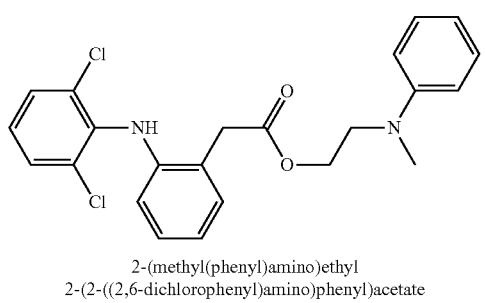

2-(methyl(phenyl)amino)ethyl
2-(2-((2,6-dichlorophenyl)amino)phenyl)acetate

DPX-1-0004

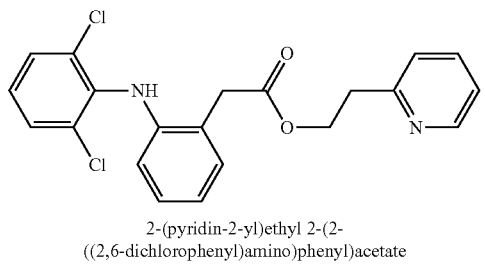

2-(pyridin-2-yl)ethyl 2-(2-
((2,6-dichlorophenyl)amino)phenyl)acetate

DPX-1-0005

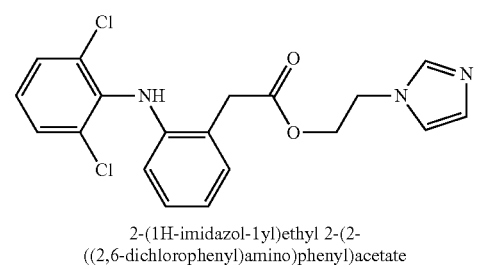

2-(1H-imidazol-1yl)ethyl 2-(2-
((2,6-dichlorophenyl)amino)phenyl)acetate

DPX-1-0006

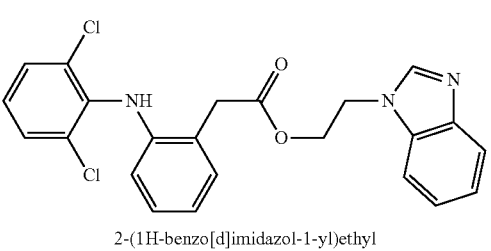

2-(1H-benzo[d]imidazol-1-yl)ethyl
2-(2-((2,6-dichlorophenyl)amino)phenyl)acetate

DPX-1-0007

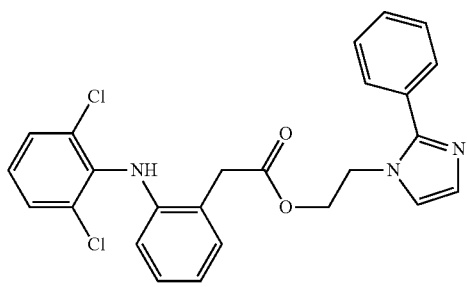

2-(2-phenyl-1H-imidazol-1yl)ethyl
2-(2-((2,6-dichlorophenyl)amino)phenyl)acetate

DPX-1-0008

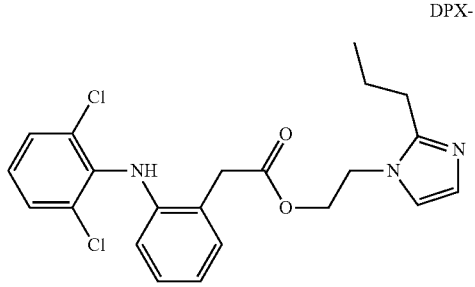

2-(2-propyl-1H-imidazol-1yl)ethyl
2-(2-((2,6-dichlorophenyl)amino)phenyl)acetate

DPX-1-0009

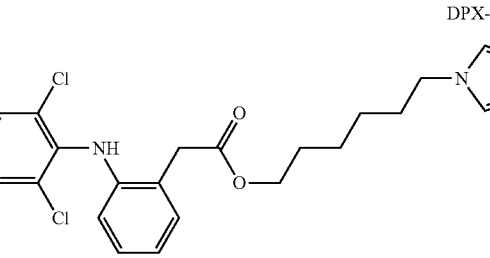

6-(1H-imidazol-1-yl)hexyl 2-(2-
((2,6-dichlorophenyl)amino)phenyl)acetate

DPX-1-0010

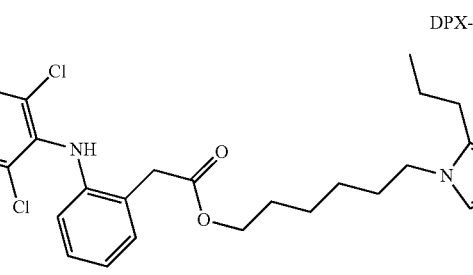

6-(2-propyl-1H-imidazol-1yl)hexyl 2-(2-
((2,6-dichlorophenyl)amino)phenyl)acetate

DPX-1-0011

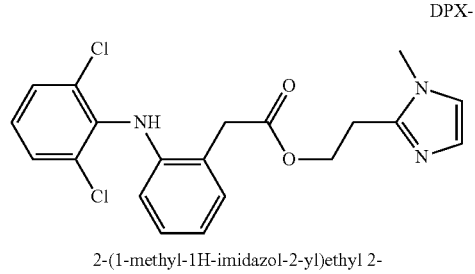

2-(1-methyl-1H-imidazol-2-yl)ethyl 2-
(2-((2,6-dichlorophenyl)amino)phenyl)acetate -continued

DPX-1-0012

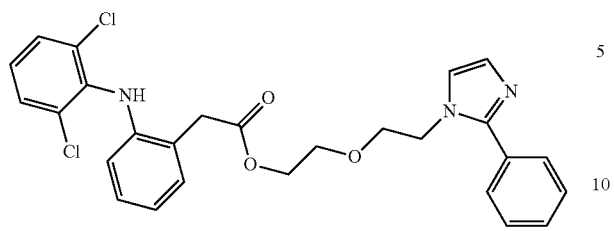

2-(2-(2-phenyl-1H-imidazol-1-yl)ethoxy)ethyl
2-(2-((2,6-dichlorophenyl)amino)phenyl)acetate Examples of prodrugs of the invention where the NSAID is naproxen:

DPX-2-0001

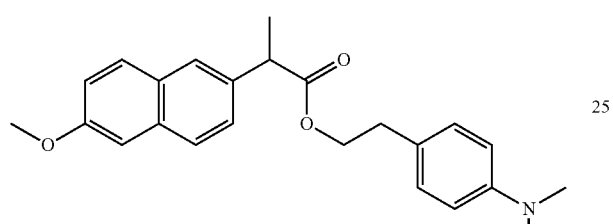

4-(dimethylamino)phenethyl
2-(6-methoxynaphthalen-2-yl)propanoate

DPX-2-0002

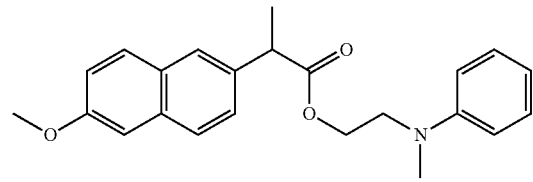

2-(methyl(phenyl)amino)ethyl
2-(6-methoxynaphthalen-2-yl)propanoate

DPX-2-0004

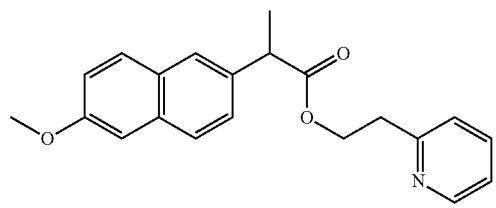

2-(pyridin-2-yl)ethyl
2-(6-methoxynaphthalen-2-yl)propanoate

DPX-2-0003

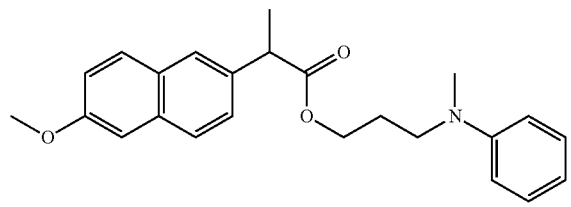

3-(methyl(phenyl)amino)propyl
2-(6-methoxynaphthalen-2-yl)propanoate

-continued

DPX-2-0005

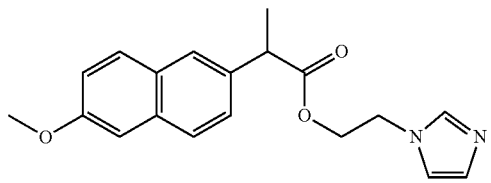

2-(1H-imidazol-1-yl)ethyl
2-(6-methoxynaphthalen-2-yl)propanoate

DPX-2-0006

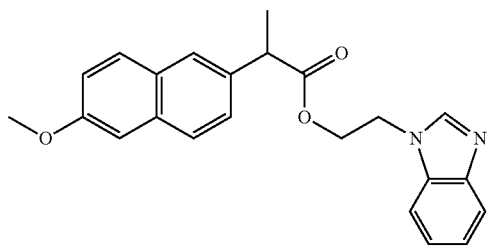

2-(1H-benzo[d]imidazol-1-yl)ethyl
2-(6-methoxynaphthalen-2-yl)propanoate

DPX-2-0007

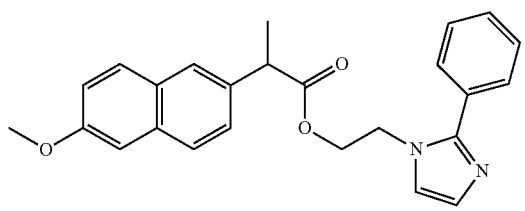

2-(2-phenyl-1H-imidazol-1-yl)ethyl
2-(6-methoxynaphthalen-2-yl)propanoate

Examples of prodrugs of the invention where the NSAID is ibuprofen:

DPX-3-0001

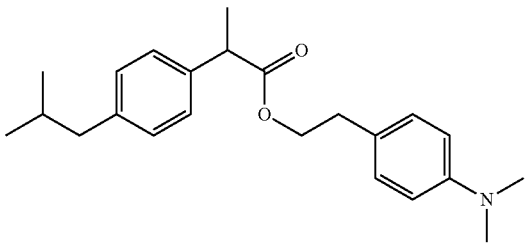

4-(dimethylamino)phenethyl
2-(4-isobutylphenyl)propanoate

DPX-3-0002

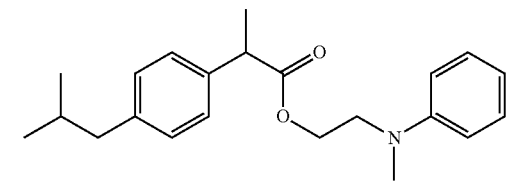

2-(methyl(phenyl)amino)ethyl
2-(4-isobutylphenyl)propanoate

DPX-3-0003

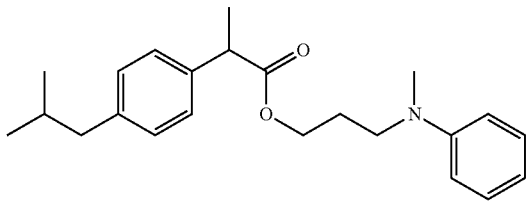

3-(methyl(phenyl)amino)propyl
2-(4-isobutylphenyl)propanoate

DPX-3-0004

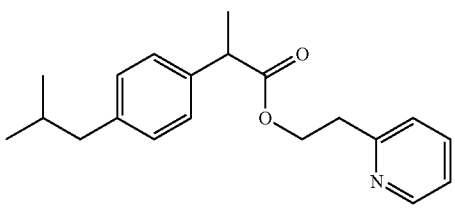

2-(pyridin-2-yl)ethyl
2-(4-isobutylphenyl)propanoate

DPX-3-0006

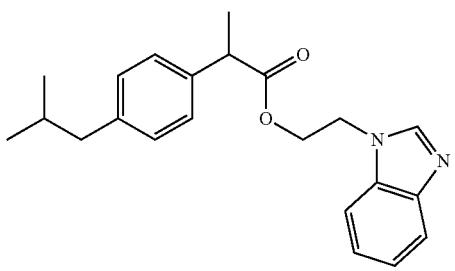

2-(1H-benzo[d]imidazol-1-yl)ethyl
2-(4-isobutylphenyl)propanoate

DPX-3-0007

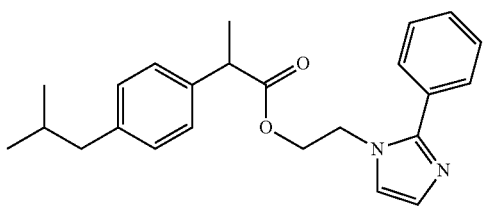

2-(2-phenyl-1H-imidazol-1-yl)ethyl
2-(4-isobutylphenyl)propanoate

Examples of prodrugs of the invention where the NSAID is ketorolac:

DPX-4-0001

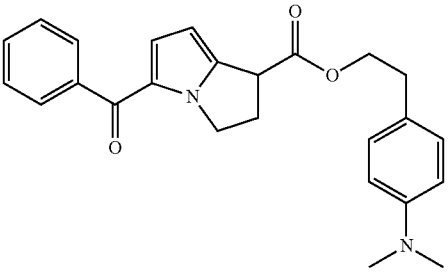

4-(dimethylamino)phenethyl 5-benzoyl-2,3-dihydro-1H-pyrrolizine-1-carboxylate

Typical ways of making prodrugs of the formula (I) is by esterification of an IPU, i.e. $R_1(-OH)_x$ with the corresponding carboxylic acid (HO—(C=O)—$R_2$) of an active pharmaceutical ingredient (API). However, many other ways of preparing prodrugs of formula (I), i.e. containing an IPU linked to one or more API through ester linkage(s). The ester prodrugs were synthesized using two different methods: Reaction of NSAID acid chlorides with IPU-alchohols or coupling of NSAID carboxylic acids with IPU-alcohols using a dehydrating agent as dicyclocarbodiimide (DCC) or 1-ethyl-3-(3-dimethylaminopropyl)carbodiimide (EDC). Conceivably the prodrugs can also be made from the NSAID carboxylic acid and an alkylation agent under the influence of a suitable base or via acid catalyzed esterification of a NSAID carboxylic acid with and IPU-alcohol.

In some embodiments the prodrug of formula (I) is a codrug, i.e. where the IPU and the API both belong to the class of active pharmaceutical ingredients. In this case the IPU is then an active pharmaceutical ingredient on its own, as opposed to just being an immobility promoting unit. In some embodiments the prodrug of formula (I) excludes codrugs.

When the prodrug is soluble, it forms a solution, which is a homogeneous mixture composed of only one phase. When the prodrug precipitates, it forms a heterogeneous mixture composed of a solid phase (e.g. a semi-solid phase) and a liquid phase, where only part of the prodrug is in solution and the rest has precipitated out as a solid (e.g. semi-solid). The solid precipitate may form a crystalline or an amorphous solid.

The solubility of the prodrug of formula (I) at a pH value that is between 2 to 6 units lower than the pH of the physiological fluid it is to be injected into, normally exceeds the corresponding solubility in the physiological fluid it is injected into by at least a factor of 100. Preferably, the solubility is at least 500, such as at least 1000, for example at least 1500 or 2000 times higher than the corresponding solubility in the physiological fluid it is injected into. The physiological fluid may be the synovial fluid, and the volume injected into the synovial fluid may correspond to between 2 and 10% (v/v) or greater of the volume of the synovial fluid. Suitable volumes are normally between 100 µl and up to 2 ml.

A simple way of testing if the solubility is indeed at least 100 times higher than the corresponding solubility in the physiological fluid it is injected into, is to first measure the pH of the physiological fluid that the prodrug of formula (I) is to be injected into. A saturated solution of the prodrug to be measured is made in an aqueous solution at a pH that is between 2 to 6 units lower than the physiological fluid it is to be injected into. Different volumes of this saturated solution is then injected into an aqueous solution at the pH of the physiological fluid that the prodrug is to be injected into, and it is measured if any precipitation occurs, e.g. visually or by other means.

The determination of the solubility of a prodrug at different pH values of interest according to the present invention is carried by adding excess solid prodrug to a container containing a buffer solution with well-defined pH. The mixture is rotated at constant temperature until an equilibrium between solid prodrug and prodrug in solution has established (that is until the prodrug concentration in the supernatant remains constant). At each measurement the pH of the supernatant is controlled and, if needed, adjusted to the desired pH. In a similar manner the solubility of a prodrug in a tissue fluid including the synovial fluid can be determined. The latter procedure comprises a simple way of testing if the solubility at the selected lower pH is indeed at least 100 times higher than the corresponding solubility in the physiological fluid it is injected into. In fact the solubility of DPX-4-0001 amounts to 65 µg/ml at pH 2.02 whereas the solubility of the prodrug decreases 1300-fold to about 0.05 µg/ml at pH 7.4. In contrast the solubility of DPX-2-0007 (derived from another IPU) was determined to approximately 7 mg/ml at pH 3.4 whereas the solubility decreased to 7 µg/ml at pH 7.4. These different pH dependent solubilities may be explained by different pKa values of the prodrugs. For instance, a decrease in pH from pH 7.4 to 2.0 will result in a 1000-fold increase in the solubility of a base with a pKa value of 5, whereas the solubility will increase by a factor of 9618 for a base with a pKa value of 6. These predicted alterations in pH dependent solubilities can be calculated from the expression: $S_t = S_0 * (1+10^{pKa-pH})$ where $S_t$ is the total solubility at a given pH and $S_0$ is the solubility of the neutral form of the prodrug.

Preferably the bodily fluid at physiological pH is synovial fluid, which is found in the synovial cavity of synovial joints. Physiological pH in this case refers to the intra-articular pH of synovial fluid, which may be from pH 6 to pH 8. In cases not involving acidosis the typical values are from pH 7.0 to 7.6, for example between pH 7.2 to 7.5, such as pH 7.3 to 7.45, for example 7.3, 7.35, 7.4.

In another aspect, the invention provides a pharmaceutical composition, which contains a therapeutically effective amount of a compound according to the present invention, and at least one pharmaceutically acceptable carrier, vehicle and/or adjuvant.

The prodrug of formula (I) may be dissolved in an aqueous vehicle and the solution is made slightly acidic by addition of a calculated amount of an appropriate acid, such as hydrochloric acid to provide a pharmaceutical composition. Such pharmaceutical composition would also be suitable for intra-articular injection. Optionally, a suitable cosolvent might be added to optimize prodrug solubility. Examples of suitable cosolvents are N,N-dimethylacetamide, N-methylpyrrolidone, dimethylsulphoxide (DMSO), polyethylene glycol (PEG 200, PEG 400), propylene glycol, isopropanol, propanol, ethanol and mixtures thereof.

Further, the composition may comprise a dry powder of the prodrug of formula (I) or salt of prodrug to be reconstituted in an appropriate aqueous vehicle just prior to injection.

In some embodiments of the invention, the compounds or pharmaceutical compositions are for use as a medicament, and in other embodiments of the invention, for use in treatment of inflammation in joints, for use in treatment of osteoarthritis and analogous affections. In yet further embodiments the compounds or pharmaceutical compositions are for use in the treatment of postoperative pain following arthroscopic surgery.

The novel compounds and the pharmaceutical compositions of the present invention may be used in medicine such as, e.g. in the treatment of postoperative pain/inflammation following arthroscopic procedures as well as in the management of inflammation in joints or in osteoarthritis associated pain and may accordingly be designed in a form that is suitable for intra-articular injection.

Treating the pathological condition postoperative pain following arthroscopic surgery, involves the treatment of both inflammation and pain, which means that at least one type of API covalently attached to an IPU with an ester bond is relevant, preferably selected from NSAIDs.

In another aspect, the invention provides a method for the preparation of a novel prodrug according to the invention and a method for the preparation of a medicament with anti-inflammatory and pain relieving activity, characterized in that it comprises a prodrug according to the present invention and one or more pharmaceutically acceptable excipients.

Treating the pathological condition inflammation in joints, such as osteoarthritis and analogous affections, involves the treatment of both inflammation and pain which means that at least one type of API covalently attached to an IPU with an ester bond is relevant, preferably selected from NSAIDs The prodrugs of formula (I) may be used in mammals, preferably humans, horses and dogs.

When describing the embodiments and aspects of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

Another aspect of the invention is a compound of formula (II):

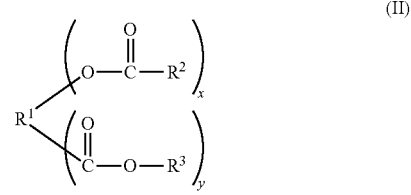

(II)

wherein $R^1$ represents an immobility promoting unit selected from an organic moiety with a molecular weight lower than 1500 g/mol such as lower than 1000 g/mol comprising one or more nitrogen containing moieties each with a p$K_a$ of between 4 and 7.4 at 37° C.; —O—(C=O)—$R^2$ represents a acyloxy residue of a carboxylic acid group containing active pharmaceutical ingredient, preferably a non-steroidal anti-inflammatory agent or an immunosuppressant; —O—$R^3$ represents a hydroxyl residue of a hydroxyl group containing active pharmaceutical agent, preferably an opiate or a corticosteroid; x is an integer selected from 0, 1, 2, 3 or 4; y is an integer selected from 0, 1, 2, 3 or 4; where the sum x+y is at least 1; and pharmaceutically acceptable salts, solvates and hydrates thereof.

All details with respect to the group $R^1$ and $R^2$ is the same as the details described hereinbefore for $R_1$ and $R_2$, respectively, and all details regarding the compounds of formula I also applies for the compounds of formula II. Especially, when y=0 the compound of formula II is the same as a compound of formula I.

Formula II represents compounds where the principle also is applied to drug substances having —OH as a functional group. Thus, the hydroxyl group containing active pharmaceutical ingredient may be selected from the list consisting of: prednisolone, methylprednisolone, triamcinolone and dexamethasone, or it may be selected from the list consisting of: codeine, morphine, oripavine, dihydrocodeine, hydromorphone, oxycodone, oxymorphone, ohmefentanyl, ketobemidone, dezocine, pentazocine, phenazocine, buprenorphine, dihydroetorphine, etorphine, butorphanol, nalbuphine, levorphanol, meptazinol, tramadol, tapentadol.

In preferred aspects y is 0 or y is 1 and x is 1.

With respect to the structure for $R^1$, the structures are similar to the structures described herein for the main aspect of the invention (formula I), but where the —OH group is replaced by a —COOH group.

All particulars and details described herein for the main aspect apply in its entirety to the aspect relating to formula II.

BRIEF DESCRIPTION OF THE DRAWING

FIG. 2. The time course for DPX-4-0001 (ALE 408) and ketorolac in solution after addition of solid DPX-4-0001 (ALE 408) to synovial fluid at 37° C. illustrating the cleavage of dissolved prodrug to the active substance.

FIG. 3. Precipitation of DPX-4-0001 after addition of a concentrated aqueous acidic solution to buffer pH 7.4 solution followed by non-enzymatic hydrolysis of dissolved DPX-4-0001 to ketorolac.

FIG. 4 shows factors influencing the pharmacokinetic fate of the prodrug/drug after administration of the prodrug into the joint. The prodrug dissolved is converted into the active drug by enzymatic cleavage of the prodrug bond.

Figure 1:
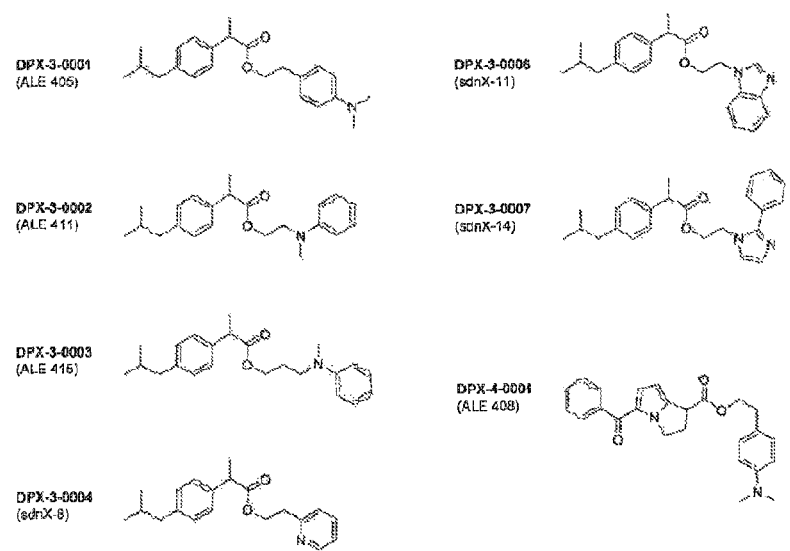
FIG. 1 shows the structures of the twenty five prodrugs with the NSAIDs ketorolac, diclofenac, ibuprofen, and naproxen attached to different immobility promoting units (IPUs) including different linker structures.

The invention is illustrated in, but not limited to, the following examples

EXAMPLES

The inventors have tested twenty five compounds/prodrugs (all promoieties comprising aniline, pyridine, imidazole and benzimidazole structures). The prodrugs were tested according to the "method for testing solubility" below. As expected, all prodrugs exhibited a low although variable solubility at pH 7.4 (due to the very low solubility of the neutral form of the prodrugs).

The structures of the twenty five prodrugs with the NSAIDs ketorolac, diclofenac, ibuprofen, and naproxen attached to different immobility promoting units (IPUs) are shown in FIG. 1.

Standard procedures were used to synthesize the ester derivatives as apparent from the more detailed description of the synthesis of the NSAID ester prodrugs presented below. Purity of the synthesized derivatives exceeded 95% as assessed by $^1$H-NMR and HPLC.

Method for Testing Solubility

The determination of the solubility of a prodrug at different pH values of interest according to the present invention is carried by adding excess solid prodrug to a container containing a buffer solution with well-defined pH. The mixture is rotated at constant temperature until an equilibrium between solid prodrug and prodrug in solution has established (that is until the prodrug concentration in the supernatant remains constant). At each measurement the pH of the supernatant is controlled and eventually adjusted to the desired pH. In a similar manner the solubility of a prodrug in a tissue fluid including the synovial fluid can be determined.

Example 1

DPX-1-0001 (ALE463)

4-(dimethylamino)phenethyl 2-(2-(2,6-dichlorophenylamino)phenyl)acetate 2-(4-(dimethylamino)phenyl)ethanol (3.3 mmol, 0.55 g), and Dichlofenac (3.3 mmol, 0.99 g) was suspended in dichloromethane (30 mL) under $N_2$ and Dicyclohexylcarbodiimid (6.6 mmol, 1.36 g), 4-Dimethylaminopyridine (0.33 mmol, 36 mg) was added. The mixture was stirred overnight before being poured into sat. $NH_4Cl$ (100 mL) and extracted with dichloromethane (4×50 mL). Drying, filtration and evaporation gave 2.4 g crude material which was purified by Flash Chromatography using EtOAc and Heptanes as eluent giving 0.65 g (43%) of the desired compound. 1H NMR (400 MHz, DMSO-d6) 7.52 (d, J=8.03 Hz, 4H), 7.13-7.24 (m, 4H), 7.04-7.10 (m, 2H), 6.93-7.02 (m, 5H), 6.85 (dt, J=1.25, 7.40 Hz, 2H), 6.58-6.63 (m, 4H), 6.26 (d, J=7.53 Hz, 1H), 4.21 (t, J=7.03 Hz, 4H), 3.78 (s, 2H), 2.82 (s, 11H), 2.77 (t, J=7.03 Hz, 4H) 13C NMR (400 MHz, DMSO-d6) 171.40, 137.07, 130.90, 129.28, 125.86, 123.20, 112.53, 65.51, 37.11, 33.40.

Example 2

DPX-1-0002 (ALE 482)

2-(methyl(phenyl)amino)ethyl 2-(2-(2,6-dichlorophenylamino)phenyl)acetate

Using an identical procedure as described for DPX-1-0001:

2-(methyl(phenyl)amino)ethanol (3.3 mmol, 0.50 g), Dichlofenac (3.3 mmol, 0.99 g), Dichclohexylcarbodiimid (6.6 mmol, 1.36 g), 4-Dimethylaminopyridine (0.3 mmol, 36 mg) and dichloromethane (30 mL). Crude yield: 1.4 g; yield after Flash Chromatography using ethyl acetate and heptanes as eluent: 0.83 g (59%). $^1$H NMR (400 MHz, DMSO-d6) d 7.52 (d, J=8.28 Hz, 3H), 7.20 (t, J=8.16 Hz, 2H), 7.10-7.15 (m, 4H), 7.05 (dt, J=1.51, 7.78 Hz, 2H), 6.97 (s, 1H), 6.83 (dt, J=1.25, 7.40 Hz, 2H), 6.66-6.72 (m, 3H), 6.56-6.63 (m, 2H), 6.25 (d, J=8.03 Hz, 1H), 4.24 (t, J=5.77 Hz, 3H), 3.74 (s, 3H), 3.58 (t, J=5.77 Hz, 3H), 2.83 (s, 5H). $^{13}$C NMR (400 MHz, DMSO-d6) δ 171.43, 148.71, 142.81, 137.06, 129.13, 128.94, 127.71, 123.02, 115.89, 111.98, 61.90, 50.24, 38.15, 37.02, 31.23, 28.34, 22.07, Methanesulfonate salt of DPX-1-0002.

Methanesulfonic acid (113 μl, 167 mg, mmol) in dry diethyl ether (10 mL) was added by syringe to a magnetically stirred solution of 2-(methyl(phenyl)amino)ethyl 2-(2-(2,6-dichlorophenylamino)phenyl)acetate (746 mg, 1.74 mmol) in dry diethyl ether (20 mL) under nitrogen cooled in an ice bath. The resulting precipitate in the form of a sticky gum was isolated by decanting off the solvent and washing the gum with dry ether (10 mL). The gum was dried under high vacuum and crystallized from ethanol to afford the title compound as a colourless solid (653 mg). Mp. 143.6-144.6° C. (dec.) (ethanol). $^1$H NMR (400 MHz, DMSO) δ 7.53 (d, J=8 Hz, 2H), 7.27-6.78 (m, 11H), 6.26 (dd, J=8.0, 1 Hz, 1H), 4.23 (t, J=5.5 Hz, 2H), 3.75 (s, 2H), 3.68 (t, J=5.5 Hz, 2H), 2.95 (s, 3H), 2.45 (s, 3H). $^{13}$C NMR (101 MHz, DMSO) δ 171.31, 142.83, 137.04, 131.01, 130.73, 129.26, 129.15, 127.76, 125.95, 122.93, 120.59, 115.83, 114.22, 61.21, 51.76, 39.70 (CH3), 36.94. DEPT $^{13}$C NMR (101 MHz, DMSO) δ 131.01, 129.27, 129.16, 127.77, 125.96, 120.60, 115.84, 61.22, 39.70, 36.94.

Example 3

DPX-1-0004 (sdnX-20)

2-(pyridin-2-yl)ethyl 2-(2-((2,6-dichlorophenyl)amino)phenyl)acetate

Using an identical procedure as described for DPX-1-0001:

2-(pyridin-2-yl)ethanol (37.7 mmol, 4.65 g), Dichlofenac (9.43 mmol, 3.0 g), 4-Dimethylaminopyridin (0.3 mmol, 35 mg), 1-Ethyl-3-(3-dimethylaminopropyl) carbodiimide-HCl (11.32 mmol, 2.17 g), Dichloromethane (15 mL) and Dimethylformamide (10 mL). Yield after Flash Chromatography using ethyl acetate and heptanes as eluent: 1.67 g. The solid HCl-salt was prepared by passing a stream of HCl through an ethereal solution of the product. $^1$H NMR (CDCl$_3$) 3.3-3.7 (m, 4H), 4.58 (br s, 2H), 6.24-7.30 (m, 8H), 7.60 (br s, 1H), 7.97 (br s, 1H), 8.57 (br s, 1H). $^{13}$C (CDCl$_3$): 13.76, 22.29, 25.24, 28.61, 30.62, 31.47, 32.39, 38.03, 62.30, 67.58, 111.37, 121.53, 123.17, 124.30, 124.77, 127.39, 127.81, 128.51, 128.59, 129.42, 130.78, 136.85, 140.77, 142.26, 145.15, 153.05.

Example 4

DPX-1-0005 (ALE460-2)

2-(1H-imidazol-1-yl)ethyl 2-(2-(2,6-dichlorophenylamino)phenyl)acetate

Using an identical procedure as described for DPX-1-0001;

2-(1H-imidazol-1-yl)ethanol (12 mmol, 1.3 g), Dichlofenac (6 mmol, 1.77 g), Dimethylaminopyridin (0.3 mmol, 22 mg), Dicyclohexylcarbodiimid (7.2 mmol, 1.5 g) and Dichloromethane (50 mL). Crude yield: 2.13 g; yield after Flash Chromatography using ethyl acetate and heptanes as eluent: 0.80 g (34%). $^1$H NMR (400 MHz, DMSO-d6) d 7.58 (t, J=1.00 Hz, 3H), 7.50-7.55 (m, 6H), 7.13-7.27 (m, 7H), 7.09 (t, J=1.25 Hz, 3H), 7.06 (dt, J=1.51, 7.65 Hz, 3H), 7.02 (s, 3H), 6.81-6.87 (m, 6H), 6.24 (d, J=7.53 Hz, 1H), 4.30-4.35 (m, 6H), 4.21-4.26 (m, 6H), 3.82 (s, 2H)$^{13}$C NMR (400 MHz, DMSO-d6) 171.14, 142.85, 137.46, 130.92, 129.13, 127.75, 122.80, 120.50, 119.58, 115.70, 63.98, 45.02, 36.74, 33.33.

Example 5

DPX-1-0006 (JBX022)

2-(1H-benzo[d]imidazol-1-yl)ethyl 2-(2-((2,6-dichlorophenyl)amino)phenyl)acetate 1-Ethyl-3-(3-dimethylaminopropyl)carbodiimide-HCl (1.10 g, 5.74 mmol) was added solid all at once to a magnetically stirred solution of diclofenac (1.48 g, 5.00 mmol), 2-(1H-benzo[d]imidazol-1-yl)ethanol (0.810 g, 10.0 mmol) and 4-Dimethylaminopyridine (31 mg, 0.25 mmol) in dry Tetrahydrofuran (30 mL) cooled in an ice bath and kept under nitrogen. The reaction mixture was stirred in an ice bath for 1 hour and then at ambient temperature. After stirring for 24 hours at room temperature the mixture was concentrated and the residue partitioned between water (25 mL), saturated NH$_4$Cl (25 mL) and EtOAc (100 mL). The organic layer was washed with 50% saturated NH$_4$Cl (2×40 mL), 50% saturated NaHCO$_3$ (40 mL) and brine (50 mL). The organic layer was dried and concentrated. Flash Chromatography using ethyl acetate and heptanes as eluent afforded a colourless oil that crystallised from ether (1.53 g) and was recrystallised to afford the title compound as a colourless solid (1.25 g, 57%). Mp. 128.8-129.3° C. (EtOAc-heptane). $^1$H NMR (400 MHz, DMSO) δ 8.15 (s, 1H), 7.65-7.60 (m, 2H), 7.51 (d, J=8.0 Hz, 2H), 7.29-7.15 (m, 3H), 7.09-7.01 (m, 2H), 6.94 (s, 1H), 6.80 (td, J=7.5, 1.0 Hz, 1H), 6.23 (d, J=8.0 Hz, 1H), 4.54 (t, J=5.0 Hz, 2H), 4.44 (t, J=5.0 Hz, 2H), 3.75 (s, 2H). $^{13}$C NMR (101 MHz, DMSO) δ 171.13, 144.16, 143.31, 142.82, 137.02, 133.85, 130.90, 130.86, 129.08, 127.74, 125.95, 122.74, 122.31, 121.46, 120.50, 119.38, 115.74, 110.31, 63.21, 43.20, 36.75. $^{13}$C-DEPT NMR (101 MHz, DMSO) δ 144.17, 130.90, 129.09, 127.74, 125.96, 122.32, 121.46, 120.50, 119.38, 115.74, 110.31, 63.21, 43.20, 36.75.

Example 6

DPX-1-0007 (sdnX-18)

2-(2-phenyl-1H-imidazol-1-yl)ethyl 2-(2-((2,6-dichlorophenyl)amino)phenyl)acetate The required IPU: 2-(2-phenyl-1H-imidazol-1-yl)ethanol was prepared in the following way: A magnetically stirred solid mixture 2-phenylimidazole (37.7 g, 0.261 mol) and ethylene carbonate (28.8 g, 0.327 mol) in a 250 mL three necked flask round bottomed flask equipped with a bubble tube and an internal thermometer was heated in a oil bath to 130-140° C. were evolution of CO$_2$ started. The mixture was kept at this temperature until evolution of CO$_2$ ceased. More ethylenecarbonate in portions of 2-3 g was added and the mixture reheated until evolution of CO$_2$ ceased or full conversion of 2-phenylimidazole as indicated by TLC was achieved. The dark brown mixture was cooled to room temperature and dissolved in water (100 mL) and extracted with ethyl acetate (3-4×100 mL). The combined organic layers were washed with brine (100 mL) and dried over Na$_2$SO$_4$. Concentration gave a dark brown oily residue (37.7 g) which was crystallised from EtOAc-heptane to give 21.5 g of a brown solid. This material was recrystallised from EtOAc-EtOH to afford the title compound as a pale brown solid in sufficient purity to be used in subsequent steps without further purification (18.7 g, 38%).

DPX-1-0007 was subsequently prepared using an identical procedure as described for DPX-1-0001: 2-(2-phenyl-1H-imidazol-1-yl)ethanol (12 mmol, 2.26 g), Dichlofenac (6 mmol, 1.77 g), 4-Dimethylaminopyridin (0.3 mmol, 22 mg), Dicyclohexylcarbodiimid (7.2 mmol, 1.5 g) and dichloromethane (50 mL). $^1$H NMR (400 MHz, DMSO) δ 7.61-7.56 (m, 2H), 7.52 (d, J=8.1 Hz, 2H), 7.48-7.36 (m, 3H), 7.29 (d, J=1.2 Hz, 1H), 7.23-7.17 (m, 1H), 7.10-7.02 (m, 2H), 6.96 (d, J=1.2 Hz, 1H), 6.91 (s, 1H), 6.83 (td, J=7.4, 1.1 Hz, 1H), 6.23 (d, J=7.8 Hz, 1H), 4.38-4.27 (m, 4H), 3.69 (s, 2H).

Example 7

DPX-1-0008 (ALE459-3)

2-(2-propyl-1H-imidazol-1-yl)ethyl 2-(2-(2,6-dichlorophenylamino)phenyl)acetate.

Using an identical procedure as described for DPX-1-0001:

Dichlorfenac (6 mmol, 1.7 g), 6-(1H-imidazol-1-yl)ethan-1-ol (12 mmol, 1.8 g), Dicyclohexylcarbidiimide (7.2 mmol, 1.4 g), 4-Dimethylaminopyridine (0.6 mmol, 72 mg) and dichloromethane (50 mL) Crude yield: 3.6 g; yield after Flash Chromatography using ethyl acetate and heptanes as eluent: 1.2 g (46%). $^1$H NMR (400 MHz, DMSO-d6) d 7.52 (d, J=8.03 Hz, 5H), 7.20 (t, J =8.03 Hz, 2H), 7.14 (dd, J=1.51, 7.53 Hz, 2H), 7.06 (dt, J=1.51, 7.78 Hz, 2H), 6.95-7.01 (m, 4H), 6.84 (dt, J=1.13, 7.47 Hz, 2H), 6.70 (d, J=1.25 Hz, 2H), 6.25 (d, J=7.78 Hz, 1H), 4.26-4.35 (m, 2H), 4.10-4.17 (m, 2H), 3.80 (s, 2H), 1.63 (dquin, J=7.28, 7.47 Hz, 2H), 0.90 (t, J=7.40 Hz, 3H). $^{13}$C NMR (400 MHz, DMSO-d6) 171.15, 147.40, 142.85. 130.92, 130.82, 129.13, 127.77,126.48, 125.98, 122.82, 119.44, 115.81, 63.95, 43.69, 27.65, 20.85, 13.75.

Example 8

DPX-1-0009 (ALE480-1)

6-(1H-imidazol-1-yl)hexyl 2-(2-(2,6-dichlorophenylamino)phenyl)acetate

Using an identical procedure as described for DPX-1-0001:

Dichlorfenac (6 mmol, 1.7 g), 6-(1H-imidazol-1-yl)hexan-1-ol (6 mmol, 1.0 g) Dicyclohexylcarbidiimide (12 mmol), 4-Dimethylaminopyridine (0.6 mmol, 72 mg) dichloromethane (50 mL). Crude yield: 2.1 g; yield after Flash Chromatography using ethyl acetate and heptanes as eluent: 0.5 g (20%). $^1$H NMR (400 MHz, DMSO-d6) 7.46-7.66 (m, 5H), 7.16-7.25 (m, 3H), 7.12 (s, 2H), 7.02-7.08 (m, 3H), 6.81-6.88 (m, 3H), 6.26 (d, J=7.78 Hz, 1H), 4.03-4.08 (m, 4H), 3.89 (t, J=7.03 Hz, 3H), 3.79 (s, 2H), 1.64 (quin, J=7.28 Hz, 3H), 1.56 (ddt, J=6.78, 7.03, 7.15 Hz, 3H), 1.22-1.33 (m, 4H), 1.14-1.22 (m, 4H). $^{13}$C NMR (400 MHz, DMSO-d6) 171.53, 142.73, 137.06, 129.15, 128.28, 127.67, 125.85, 123.30, 119.15, 115.89, 64.38, 45.75, 37.10, 30.40, 27.92, 25.49, 24.74.

Example 9

DPX-1-0010 (ALE481-2)

6-(2-propyl-1H-imidazol-1-yl)hexyl 2-(2-(2, 6-dichlorophenylamino) phenyl)acetate Using an identical procedure as described for DPX-1-0001:

Dichlorfenac (6 mmol, 1.4 g), 6-(2-propyl-1H-imidazol-1-yl)hexan-1-ol (6 mmol, 1.25 g), Dicyclohexylcarbidiimide (12 mmol, 2.4 g), 4-Dimethylaminopyridin (0.6 mmol, 72 mg) and dichloromethane (60 mL). Crude yield: 1.9 g; yield after Flash Chromatography using ethyl acetate and heptanes as eluent: 0.21 g (10%). $^1$H NMR (400 MHz, DMSO-d6) d 7.52 (d, J=8.03 Hz, 1H), 7.13-7.27 (m, 1H), 6.94-7.09 (m, 2H), 6.81-6.88 (m, 1H), 6.72 (d, J=1.00 Hz, 1H), 6.27 (s, 1H), 4.06 (t, J=6.53 Hz, 2H), 3.72-3.83 (m, 3H), 1.50-1.73 (m, 4H), 1.15-1.36 (m, 3H), 0.91 (t, J=7.40 Hz, 2H). $^{13}$C NMR (400 MHz, DMSO-d6) d 171.52, 146.91, 142.2, 137.06, 130.84, 130.52, 129.15, 127.66, 123.31, 119.10, 115.89, 64.38, 44.64, 30.35, 27.94, 27.79, 20.92, 13.75.

Example 10

DPX-1-0011

2-(1-methyl-1H-imidazol-2-yl)ethyl 2-(2((2,6-dichlorophenyl)amino)phenyl)acetate 1-Ethyl-3-(3-dimethylaminopropyl)carbodiimide-HCl (EDC-HCl) (0.661 g, 3.45 mmol) was added solid all at once to a magnetically stirred solution of diclofenac (0.888 g, 3.00 mmol), 2-(1-methyl-1H-imidazol-2-yl)ethanol (0.379 g, 3.00 mmol) and 4-Dimethylaminopyridine (19 mg, 0.15 mmol) in dry tetrahydrofuran (20 mL) cooled in an ice bath and kept under nitrogen. The reaction mixture was stirred in an ice-bath for 30 min and then at ambient. After stirring for 12 hrs at room temperature more EDC-HCl (115 mg, 0.6 mmol) was added and stirring was continued at room temperature for 72 hrs. The mixture was concentrated and the residue partitioned between 50% saturated $NH_4Cl$ (25 mL) and EtOAc (60 mL). The organic layer was washed with 50% saturated $NH_4Cl$ (2×25 mL), 50% saturated $NaHCO_3$ (25 mL) and brine (30 mL). The organic layer was dried over $Na_2SO_4$ and concentrated. Flash Chromatography using ethyl acetate and heptanes as eluent provided the title compound which crystallised from heptane as a colorless solid (196 mg). Mp. 114.5-115.2° C. (EtOAc-Heptane). $^1$H NMR (400 MHz, DMSO) δ 7.53 (d, J=8.1 Hz, 2H), 7.24-7.18 (m, 1H), 7.17 (dd, J=7.5, 1.4 Hz, 1H), 7.10 (s, 1H), 7.06 (td, J=7.8, 1.5 Hz, 1H), 6.99 (d, J=1.2 Hz, 1H), 6.83 (td, J=7.4, 1.1 Hz, 1H), 6.71 (d, J=1.2 Hz, 1H), 6.24 (d, J=7.4 Hz, 1H), 4.39 (t, J=7.0 Hz, 2H), 3.79 (s, 2H), 3.52 (s, 3H), 2.98 (t, J=7.0 Hz, 2H). $^{13}$C NMR (101 MHz, DMSO) δ 171.37, 144.11, 142.93, 137.08, 130.98, 130.94, 129.12, 127.72, 126.27, 126.03, 122.91, 121.13, 120.45, 115.63, 62.61 (CH2), 37.08 (CH2), 32.07, 25.48 (CH2). DEPT-$^{13}$C NMR (101 MHz, DMSO) δ 130.95, 129.12, 127.73, 126.27, 126.03, 121.13, 120.44, 115.62, 62.61, 37.07, 32.07, 25.48.

Example 11

DPX-1-0012

2-(2-(2-phenyl-1H-imidazol-1-yl)ethoxy)ethyl 2-(2-((2,6-dichlorophenyl)-amino)phenyl)acetate The required IPU: 2-(2-(2-phenyl-1H-imidazol-1-yl)ethoxy)ethanol was obtained as a byproduct in the synthesis of another IPU: 2-(2-phenyl-1H-imidazol-1-yl)ethanol (see under DPX-1-0007) in the following way: The filtrate from the initial crystallisation was purified by Flash Chromatography using EtOAc:heptane→EtOAc:MeOH as eluent and fractions containing the title compound was combined (~7 g) and recrystallised from EtOAc:heptane to give 4.56 g of pale yellow solid. This material was purified again by Flash Chromatography using EtOAc→EtOAc:MeOH (90:10) as eluent. Relevant fractions were combined and recrystallised from toluene to afford the title compound as a colourless solid (1.39 g, 2.3%). Mp. 94.4-95.1° C. (toluene). $^1$H NMR (400 MHz, DMSO) δ 7.66-7.62 (m, 2H), 7.51-7.41 (m, 3H), 7.38 (d, J=1.0 Hz, 1H), 7.00 (d, J=1.0 Hz, 1H), 4.59 (t, J=5.5 Hz, 1H), 4.17 (t, J=5.5 Hz, 2H), 3.72 (t, J=5.5 Hz, 2H), 3.49-3.42 (m, 2H), 3.40-3.35 (m, 2H). $^{13}$C NMR (101 MHz, CDCl$_3$) δ 148.19, 130.91, 129.23, 128.91, 128.72, 128.70, 121.06, 72.68, 70.58, 61.71, 46.73.

Subsequently, DPX-1-0012 was prepared in the following way: 1-Ethyl-3-(3-dimethylaminopropyl)carbodiimide-HCl (EDC-HCl) (551 mg, 2.87 mmol) was added solid all at once to a magnetically stirred solution of Diclofenac (741 mg, 2.50 mmol), 2-(2-(2-phenyl-1H-imidazol-1-yl)ethoxy)ethanol (581 mg, 2.50 mmol) and 4-Dimethylaminopyridine (16 mg, 0.13 mmol) in dry tetrahydrofuran (15 mL) cooled in an ice bath and kept under nitrogen. The reaction mixture was stirred in an ice bath for 30 min and then at ambient temperature. After stirring for 12 hours more EDC-HCl (96 mg, 0.5 mmol) was added and stirring was continued at room temperature for 72 hours. The mixture was concentrated and the residue partitioned between 50% saturated $NH_4Cl$ (25 mL) and EtOAc (50 mL). The organic layer was washed with 50% saturated $NH_4Cl$ (2×25 mL), 50% saturated $NaHCO_3$ (25 mL) and brine (30 mL). The organic layer was dried over $Na_2SO_4$ and concentrated. The residue was purified by Flash Chromatography using ethyl acetate and heptanes as eluent to afford the title compound (274 mg) as thick pale yellow oil. $^1$H NMR (400 MHz, DMSO) δ 7.64-7.59 (m, 2H), 7.52 (d, J=8.1 Hz, 2H), 7.48-7.37 (m, 3H), 7.30 (d, J=1.2 Hz, 1H), 7.23-7.18 (m, 1H), 7.16 (dd, J=7.6, 1.4 Hz, 1H), 7.07-7.01 (m, 2H), 6.98 (d, J=1.2 Hz, 1H), 6.82 (td, J=7.4, 1.1 Hz, 1H), 6.25 (d, J=7.8 Hz, 1H), 4.17-4.09 (m, 4H), 3.78 (s, 2H), 3.69 (t, J=5.3 Hz, 2H), 3.59-3.54 (m, 2H). $^{13}$C NMR (101 MHz, DMSO) δ 171.45, 146.93, 142.81, 137.08, 130.92, 130.85, 130.63, 129.14, 128.78, 128.38, 128.30, 127.86, 127.71, 125.88, 123.12, 121.44, 120.62, 115.89, 69.61, 68.18, 63.75, 46.00, 36.94. DEPT $^{13}$C NMR (101 MHz, DMSO) δ 130.85, 129.13, 128.78, 128.38, 128.30, 127.86, 127.71, 125.88, 121.44, 120.62, 115.89, 69.60 (CH2), 68.18 (CH2), 63.75 (CH2), 46.00 (CH2), 36.94 (CH2).

Example 12

DPX-2-0001 (ALE 406)

4-(dimethylamino)phenethyl 2-(6-methoxynaphthalen-2-yl)propanoate 2-(6-methoxynaphthalen-2-yl)propanoyl chloride (acid chloride of Naproxen) (1 g, 4 mmol) was dissolved in dichloromethane (20 mL) and pyridine (30 mL) was added, and finally a solution of the 2-(4-(dimethylamino)phenyl) ethanol (0.64 g, 4 mmol) in dichloromethane (10 mL) was added. The mixture was left over night under stirring at room temperature. After addition of dichloromethane the reaction mixture was washed with first a saturated bicarbonate solution (100 mL) and second water (100 mL). The organic phase was dried and concentrated to yield an oily residue. The crude product was purified by vacuum liquid chromatography on silica (20-45 μm) using heptane (60 mL) followed by heptane-ethyl acetate (4:1 v/v) as eluent. Yield 0.52 g (35%). $^1$H NMR (300 MHz, CDCl$_3$): δ 7.70-7.64 (3H, m); 7.37 (1H, dd, J=6.60; 1.5 Hz); 7.15-7.11 (2H, m); 6.9 (2H, d, J=8.8 Hz); 6.52 (2H, d, J=8.56); 4.27 (2H, t, J=6, 88 Hz); 3.92 (3H, s); 3.84 (1H, q, J=7.15 Hz); 2.88 (6H, s); 2.76 (2H, t, J=7.15 Hz); 1.57 (3H, d, J=7.15 Hz). 13C NMR (400 MHz, DMSO-d6) δ 173.76, 157.18, 135.60, 135.60, 129.24, 126.96, 126.23, 125.73, 118.66, 105.69, 65.29, 55.15, 44.51, 33.30, 18.17.

Example 13

DPX-2-0002 (ALE 412)

2-(methyl(phenyl)amino)ethyl 2-(6-methoxynaphthalen-2-yl)propanoate

Using an identical procedure as described for DPX-2-0001 using 2-(6-methoxynaphthalen-2-yl)propanoyl chloride (1.7 g, 7.2 mmol) and 2-(methyl(phenyl)amino)ethanol (1.10 g, 7.2 mmol). Yield 0.9 g (36%). $^1$H NMR (300 MHz, CDCl$_3$): δ 7.7 (3H, d, J=8.53 Hz); 7.62 (1H, d, J=1.38 Hz); 7.35 (1H, dd, J=8; 1.65 Hz); 7.22-7.10 (2H, m), 6.69 (3H, m); 4.23 (2H, t, J=5.78); 3.92 (3H, s); 3.80 (1H, q, J=7.15 Hz); 3.53 (2H, t, J=5.78 Hz); 2.83 (3H, s); 1.54 (3H, d, J=6.88 Hz). $^{13}$C NMR (400 MHz, DMSO-d6) δ 173.87, 157.17, 135.53, 133.31, 128.92, 126.94, 126.64, 118.71, 115.88, 111.91, 105.70, 61.80, 55.14, 50.18, 44.50, 38.06, 18.22.

Example 14

DPX-2-0003 (ALE 416)

3-(methyl(phenyl)amino)propyl 2-(6-methoxynaphthalen-2-yl)propanoate

Using an identical procedure as described for DPX-2-0001 using 2-(6-methoxynaphthalen-2-yl)propanoyl chloride (1.7 g, 7.14 mmol) and 3-(methyl(phenyl)amino)propan-1-ol (1.19 g; 7.14 mmol). Yield 1.75 g (64%). $^1$H NMR (300 MHz, CDCl$_3$): δ 7.72-7.68 (3H, m); 7.41 (1H, dd, J=6.60 Hz; 1.93 Hz); 7.17-7.10 (3H, m); 7.71-7.53 (2H, m); 4.14 (2H, t, J=6.60 Hz); 3.92 (3H, s); 3.86 (2H, t, J=7.15 Hz); 3.28-3.19 (2H, m); 3.75 (3H, s); 1.84-1.78 (2H, m) 1.605 (3H, d, J=7.15 Hz). $^{13}$C NMR (400 MHz, DMSO-d6) δ 173.84, 157.19, 148.73, 135.71, 133.34, 128.88, 126.99, 125.64, 118.75, 115.56, 111.79, 105.75, 62.10, 55.15, 48.14, 44.48, 37.55, 25.17, 18.13.

Example 15

DPX-2-0004 (sdnX9)

2-(pyridin-2-yl)ethyl 2-(6-methoxynaphthalen-2-yl)propanoate

Using an identical procedure as described for DPX-1-0001:

2-(pyridin-2-yl)ethanol (8.12 mmol, 1.00 g), Naproxen (8.93 mmol, 2.06 g), Dimethylaminopyridin (0.4 mmol, 50 mg), 1-Ethyl-3-(3-dimethylaminopropyl) carbodiimide-HCl (EDC-HCl) (12.18 mmol, 2.33 g), Acetonitrile (5 mL) and Dimethylformamide (3 mL). Crude yield: 4.3 g. The oil was purified by flash chromatography using ethyl acetate and heptanes as eluent to give a colorless oil. The pure oil was dissolved in diethyl ether (50 mL) and 2M HCl in diethyl ether (500 uL) was added. After drying under oil pump vacuum, white crystals precipitated. $^1$H (CDCl$_3$) 1.52 (d, 2H), 3.02 (t, 2H), 3.91-3.95 (m, 1H), 3.98 (s, 3H), 4.36-4.41 (m, 2H), 6.60 (d, 1H), 7.00-7.04 (m, 1H), 7.12-7.19 (m, 2H), 7.24-7.29 (m, 1H), 7.45 (dd, 1H), 7.60 (s, 1H), 7.16-7.20 (m, 2H), 8.46-8.49 (m, 1H). $^{13}$C (CDCl$_3$) 105.53, 118.86, 121.35, 123.32, 125.95, 126.19, 127.02, 128.88, 129.25, 133.63, 135.62, 136.03, 149.26, 157.60, 157.84, 174.39.

Example 16

DPX-2-0005 (JBX019)

2-(1H-benzo[d]imidazol-1-yl)ethyl 2-(6-methoxynaphthalen-2-yl)propanoate

1-Ethyl-3-(3-dimethylaminopropyl)carbodiimide-HCl (EDC-HCl) (2.20 g, 11.5 mmol) was added solid all at once to a magnetically stirred solution of naproxen (2.30 g, 10.0 mmol), 1-(2-hydroxyethyl)imidazole (1.12 g, 10.0 mmol)

and 4-Dimethylaminopyridine (61 mg, 0.5 mmol) in dry tetrahydrofuran (50 mL) cooled in an ice bath and kept under nitrogen. The reaction mixture was stirred in an ice bath for 30 min and at ambient temperature. More EDC-HCl (400 mg, 2 mmol) was added after 13 hrs, 17 hrs. After stirring for 22 hrs at room temperature the mixture was concentrated and the residue partitioned between water (50 mL), saturated NH$_4$Cl (20 mL) and EtOAc (120 mL). The organic layer was washed with 50% saturated NH$_4$Cl (2×50 mL), 50% saturated NaHCO$_3$ (50 mL) and brine (50 mL). The organic layer was dried and concentrated. The oily residue was purified by Flash Chromatography using ethyl acetate and heptanes as eluent afforded a colourless oil (2.74 g, 84%) after drying in high vacuum. The oil was crystallised from ether and recrystallised from Tert-butylmethylether (~20 mL, seeded) to afford the title compound as a colourless solid (2.21 g, 68.3%). Mp. 60.6-61.3° C. $^1$H NMR (400 MHz, DMSO) δ 7.80 (d, J=9.0 Hz, 1H), 7.77 (d, J=8.5 Hz, 1H), 7.68 (d, J=1 Hz, 1H), 7.51 (s, 1H), 7.33 (dt, J=5.5, 3 Hz, 1H), 7.30 (d, J=2.5 Hz, 1H), 7.17 (dd, J=9, 2.5 Hz, 1H), 6.98 (t, J=1 Hz, 1H), 6.78 (t, J=1 Hz, 1H), 4.34-4.12 (m, 4H), 3.92 (q, J=7 Hz, 1H), 3.88 (s, 3H), 1.45 (d, J=7 Hz, 3H). $^{13}$C NMR (101 MHz, DMSO) δ 173.52, 157.19, 137.40, 135.30, 133.33, 129.15, 128.37, 128.25, 126.99, 126.20, 125.63, 119.46, 118.73, 105.69, 63.74, 55.15, 44.94, 44.35, 18.19.

Example 17

DPX-2-0006 (JBX017)

2-(1H-benzo[d]imidazol-1-yl)ethyl 2-(6-methoxynaphthalen-2-yl)propanoate

1-Ethyl-3-(3-dimethylaminopropyl)carbodiimide-HCl (EDC-HCl) (2.20 g, 11.5 mmol) was added solid all at once to a magnetically stirred solution of naproxen (2.30 g, 10.0 mmol), 2-(1H-benzo[d]imidazol-1-yl)ethanol (1.62 g, 10.0 mmol) and 4-Dimethylaminopyridine (68 mg, 0.5 mmol) in dry tetrahydronfuran (50 mL) cooled in an ice bath and kept under nitrogen. The reaction mixture (slurry-EDC-HCl failed to dissolve) was stirred in an ice bath for 30 min and at ambient temperature. More EDC-HCl (400 mg, 2 mmol) was added after 3, 5 and 6 hours. After stirring for 48 hours the mixture was concentrated and the residue partitioned between water (50 mL), saturated NH$_4$Cl (20 mL) and EtOAc (120 mL). The organic layer was washed with 50% saturated NH$_4$Cl (2×50 mL), 50% saturated NaHCO$_3$ (50 mL) and brine (50 mL). The organic layer was dried and concentrated. Flash Chromatography using ethyl acetate and heptanes as eluent afforded the title compound as a colourless solid (3.33 g, 88.8% yield). Mp. 125.0-125.7° C. $^1$H NMR (400 MHz, DMSO) δ 8.09 (s, 1H), 7.75 (d, J=9.0 Hz, 1H), 7.71 (d, J=8.5 Hz, 1H), 7.69-7.63 (m, 1H), 7.61-7.54 (m, 2H), 7.28 (d, J=2.5 Hz, 1H), 7.26-7.18 (m, 3H), 7.16 (dd, J=9, 2.5 Hz, 1H), 4.58-4.32 (m, 4H), 3.87 (s, 3H), 3.83 (q, J=7 Hz, 1H), 1.37 (d, J=7 Hz, 3H). $^{13}$C NMR (101 MHz, DMSO) δ 173.52, 157.18, 144.13, 143.29, 135.19, 133.83, 133.29, 129.13, 128.32, 126.93, 126.09, 125.58, 122.25, 121.46, 119.38, 118.69, 110.37, 105.67, 63.03, 55.15, 44.36, 43.10, 18.12. DEPT $^{13}$C NMR (101 MHz, DMSO) b 144.12, 129.13, 126.93, 126.09, 125.58, 122.25, 121.45, 119.37, 118.69, 110.36, 105.67, 63.03 (CH2), 55.14, 44.36, 43.10 (CH2), 18.12.

Example 18

DPX-2-0007 (JBX018)

2-(2-phenyl-1H-imidazol-1-yl)ethyl 2-(6-methoxynaphthalen-2-yl)propanoate

1-Ethyl-3-(3-dimethylaminopropyl)carbodiimide-HCl (EDC-HCl) (2.20 g, 11.5 mmol) was added solid all at once to a magnetically stirred solution of naproxen (2.30 g, 10.0 mmol), (1.88 g, 10.0 mmol) and 4-Dimethylaminopyridine (61 mg, 0.5 mmol) in dry tetrahydrofuran (50 mL) cooled in an ice bath and kept under nitrogen. The reaction mixture (slurry-EDC-HCl failed to dissolve) was stirred in an ice bath for 30 min and at ambient temperature. More EDC-HCl (400 mg, 2 mmol) was added after 13 hrs and 17 hrs. After stirring for 22 hours at room temperature full conversion of naproxen was obtained. The mixture was concentrated and the residue partitioned between water (50 mL), saturated NH$_4$Cl (20 mL) and EtOAc (120 mL). The organic layer was washed with 50% saturated NH$_4$Cl (2×50 mL), 50% saturated NaHCO$_3$ (50 mL) and brine (50 mL). The organic layer was dried and concentrated. Flash Chromatography using ethyl acetate and heptanes as eluent afforded the title compound as a pale yellow oil. $^1$H NMR (400 MHz, DMSO) δ 7.77 (d, J=9.0 Hz, 1H), 7.74 (d, J=8.6 Hz, 1H), 7.61 (d, J=1.4 Hz, 1H), 7.58-7.51 (m, 2H), 7.45-7.38 (m, 3H), 7.29 (d, J=2.5 Hz, 1H), 7.24 (dd, J=8.5, 1.8 Hz, 1H), 7.19-7.13 (m, 2H), 6.90 (d, J=1.2 Hz, 1H), 4.37-4.20 (m, 4H), 3.86 (s, 3H), 3.77 (q, J=7.1 Hz, 1H), 1.36 (d, J=7.1 Hz, 3H).

HCl-salt of DPX-2-0007: 571 mg of this oil was dissolved in a mixture of dry ether (20 mL) and dry tetrahydrofuran (10 mL) under nitrogen at 0° C. 2M HCl in ether (4 mL, 8 mmol) was added drop wise by syringe resulting in the formation a sticky gum. The solvent was decanted off and the gum was washed with dry ether (20 mL). The gum was dried in high vacuum and then crystallised by dissolving it in ethanol (2 mL) and slowly adding dry diethyl ether until no more solid formed. The free flowing solid was dried in vacuum to afford the title compound (452 mg) as an off white solid. Mp. 188.5-189.6° C. (ethanol/ether). $^1$H NMR (400 MHz, DMSO) δ 15.29 (br s, 1H), 7.85 (d, J=2.0 Hz, 1H), 7.80-7.71 (m, 3H), 7.69-7.64 (m, 1H), 7.63-7.53 (m, 5H), 7.30 (d, J=2.5 Hz, 1H), 7.21-7.15 (m, 2H), 4.46-4.35 (m, 4H), 3.88 (s, 3H), 3.81 (q, J=7.0 Hz, 1H), 1.37 (d, J=7.0 Hz, 3H). $^{13}$C NMR (101 MHz, DMSO) δ 173.46, 157.20, 144.42, 135.15, 133.30, 131.88, 129.71, 129.15, 129.06, 128.32, 127.06, 125.81, 125.55, 122.90, 122.34, 119.58, 118.82, 105.77, 62.28, 55.18, 46.50, 44.11, 18.15. DEPT $^{13}$C NMR (101 MHz, DMSO) δ 131.88, 129.71, 129.15, 129.06, 127.06, 125.82, 125.56, 122.90, 119.59, 118.82, 105.77, 62.28 (CH2), 55.18, 46.50 (CH2), 44.11, 18.15.

Example 19

DPX-3-0001 (ALE405)

4-(dimethylamino)phenethyl 2-(4-isopropylphenyl)propanoate

Using an identical procedure as described for DPX-1-0001 using 2-(4-isobutylphenyl)propanoyl chloride (7.14 mmol, 1.5 g), 2-(4-(dimethylamino)phenyl) ethanol (7.0 mmol, 1.1 g), pyridine (50 mL) and dichloromethane (50 mL). Yield: 2.6 g. $^1$H NMR (400 MHz, DMSO-d6) δ 7.05-7.23 (m, 5H), 6.93 (d, J=8.53 Hz, 2H), 6.60 (d, J=8.78 Hz, 2H), 4.02-4.24 (m, 2H), 3.70 (q, J=7.03 Hz, 1H), 3.30 (s, 1H), 2.62-2.73 (m, 2H), 1.74-1.88 (m, 1H), 1.27-1.43 (m, 3H), 0.77-0.93 (m, 6H). $^{13}$C NMR (400 MHz, DMSO-d6) δ 173.78, 149.10, 139.67, 137.78, 129.27, 127.07, 126.22, 112.48, 65.19, 44.20, 33.35, 29.57, 22.16, 18.43.

Example 20

DPX-3-0002 (ALE411)

2-(methyl(phenyl)amino)ethyl 2-(4-isobutylphenyl)propanoate

Using an identical procedure as described for DPX-1-0001 using 2-(4-isobutylphenyl)propanoyl chloride (7.14 mmol, 1.6 g), 2-((4-(dimethylamino)phenyl) (methyl)amino)ethanol (7.14 mmol, 1.0 g), pyridine (50 mL) and dichloromethane (50 mL). Yield 0.62 g (25%). $^1$H NMR (400 MHz, DMSO-d6) δ 7.05-7.27 (m, 13H), 6.50-6.75 (m, 6H), 3.98-4.27 (m, 4H), 3.66 (q, J=7.28 Hz, 2H), 3.52 (t, J=5.65 Hz, 4H), 2.73 (s, 6H), 2.41 (d, J=7.28 Hz, 5H), 1.80 (td, J=6.78, 13.55 Hz, 3H), 1.27-1.36 (m, 6H), 0.74-0.92 (m, 6H). $^{13}$C NMR (400 MHz, DMSO-d6) δ 173.87, 148.63, 139.75, 137.72, 129.03, 128.92, 127.08, 111.87, 61.79, 50.14, 44.17, 38.14, 29.57, 22.11, 18.28.

Example 21

DPX-3-0003 (ALE415)

3-(methyl(phenyl)amino)propyl 2-(4-isobutylphenyl)propanoate

Using an identical procedure as described for DPX-1-0001 using 2-(4-isobutylphenyl)propanoyl chloride (7.14 mmol, 1.6 g), 3-((4-(dimethylamino)phenyl)-(methyl)amino)propan-1-ol (7.14 mmol, 1.01 g), pyridine (50 mL) and dichloromethane (50 mL). Yield 1.55 g (68%). $^1$H NMR (400 MHz, DMSO-d6) δ 7.19-7.29 (m, 4H), 7.05-7.14 (m, 9H), 6.42-6.71 (m, 6H), 3.96-4.10 (m, 4H), 3.77 (q, J=7.19 Hz, 2H), 3.18-3.23 (m, 4H), 2.73 (s, 6H), 2.41 (d, J=7.03 Hz, 5H), 1.79 (td, J=6.74, 13.36 Hz, 2H), 1.68-1.75 (m, 4H), 1.37-1.42 (m, 6H), 0.81-0.85 (m, 6H). $^{13}$C NMR (400 MHz, DMSO-d6) δ 173.84, 148.77, 139.80, 137.92, 129.09, 128.92, 127.06, 115.58, 111.83, 62.00, 48.15, 44.18, 37.66, 29.55, 25.19, 22.11, 18.20.

Example 22

DPX-3-0004 (sdnX-8)

2-(pyridin-2-yl)ethyl 2-(4-isobutylphenyl)propanoate

Using an identical procedure as described for DPX-1-0001:

Ibuprofen (1.84 g, 8.93 mmol), 2-(pyridin-2-yl)ethanol (1.00 g, 8.12 mmol), 1-Ethyl-3-(3-dimethylaminopropyl)carbodiimide-HCl (2.33 g, 12.18 mmol), 4-dimethylaminopyridine (50 mg, 0.4 mmol) in Acetonitrile (4 mL). The oil was purified by flash chromatography using ethyl acetate and heptanes as eluent to give a colorless oil. The oil was dissolved in dioxane (5 mL) and 2M HCl in diethyl ether (3 mL) was added. The mixture was evaporated and placed under oil pump vacuum. After three hours the highly viscous substance began to crystallize. $^1$H (CDCl$_3$) 0.87 (d, 6H), 1.41 (d, 3H), 1.83 (m, 1H), 2.43 (d, 1H), 3.41-3.60 (m, 3H), 4.47-4.68 (m, 2H), 6.99-7.03 (m, 5H), 7.74 (m, 1H), 7.96 (m, 1H), 8.69 (m, 1H). $^{13}$C (CDCl$_3$) 17.84, 22.27, 30.11, 32.41, 44.78, 44.88, 61.80, 124.45, 127.20, 127.33, 129.29, 137.38, 140.63, 140.72, 144.63, 153.90, 173.88.

Example 23

DPX-3-0006 (sdnX-11)

2-(1H-benzo[d]imidazol-1-yl)ethyl 2-(4-isobutylphenyl)propanoate

Using an identical procedure as described for DPX-1-0001:

Ibuprofen (2.44 g, 11.84 mmol), 2-(1H-benzo[d]imidazol-1-yl)ethanol (1.60 g, 9.87 mmol), 1-Ethyl-3-(3-dimethylaminopropyl)carbodiimide-HCl (EDC-HCl) (2.27 g, 11.5 mmol), 4-Dimethylaminopyridine (36 mg, 0.3 mmol) in Acetonitrile (4 mL). The crude oil was purified by flash chromatograph to give 1.55 g of a white solid. $^1$H (CDCl$_3$) 0.80 (d, 6H), 1.37 (d, 3H), 1.84 (m, 1H), 2.41 (d, 2H), 3.57 (m, 1H), 4.05-4.38 (m, 4H), 6.99-7.03 (m, 4H), 7.01-7.16 (m, 3H), 7.59 (s, 1H), 7.77 (m, 1H). $^{13}$C (CDCl$_3$) 18.13, 22.34, 30.10, 43.65, 44.92, 44.97, 62.38, 109.29, 120.42, 122.28, 123.09, 127.05, 129.45, 133.54, 137.02, 140.87, 143.02, 143.57, 174.22.

Example 24

DPX-3-0007 (sdnX-14)

2-(2-phenyl-1H-imidazol-1-yl)ethyl 2-(4-isobutylphenyl)propanoate

Using an identical procedure as described for DPX-1-0001:

Ibuprofen (2.01 g, 9.75 mmol), 2-(2-phenyl-1H-imidazol-1-yl)ethanol (1.54 g, 8.12 mmol), 1-Ethyl-3-(3-dimethylaminopropyl)carbodiimide-HCl (EDC-HCl) (1.87 g, 9.75 mmol), 4-Dimethylaminopyridine (50 mg, 0.4 mmol) in dichloromethane (10 mL). The crude oil was purified by flash chromatography to give 2.74 g of a yellow oil. The HCl-salt was formed by dissolving the oil in diethyl ether and adding 2M HCl in diethyl ether. $^1$H (CDCl$_3$) 0.70 (d, 6H), 1.37 (d, 3H), 1.56 (m, 1H), 2.21 (d, 2H), 3.27 (m, 1H), 3.95-4.22 (m, 2H), 6.80 (br s, 1H), 6.86-6.97 (m, 4H), 7.20-7-38 (m, 6H). $^{13}$C (CDCl$_3$) 17.99, 22.27, 25.26, 30.08, 44.75, 44.82, 47.00, 62.01, 119.61, 121.55, 121.79, 126.95, 127.01, 129.57, 129.62, 129.64, 132.36, 136.74, 141.16, 144.79, 173.69.

Example 25

DPX-40001 (ALE408)

4-(dimethylamino)phenethyl 5-benzoyl-2,3-dihydro-1H-pyrrolizine-1-carboxylate 5-benzoyl-2,3-dihydro-1H-pyrrolizine-1-carbonyl chloride (acid chloride of Ketorolac) (0.40 mmol) was dissolved in dichloromethane (4 mL) and pyridine (4 mL). 2(4-dimethylaminophenyl)ethanol (66 mg, 0.4 mmol) was added and the mixture was stirred overnight at room temperature. Standard aqueous work-up followed by Flash Chromatography gave the desired material. $^1$H NMR (400 MHz, DMSO-d6) δ 7.72-7.82 (m, 6H), 7.41-7.66 (m, 9H), 7.02 (d, J=8.78 Hz, 6H), 6.57-6.86 (m, 8H), 5.99 (d, J=4.02 Hz, 1H), 4.32-4.41 (m, 1H), 4.24 (t, J=6.78 Hz, 2H), 4.16 (dd, J=6.27, 8.53 Hz, 1H), 2.83 (s, 6H), 2.76-2.81 (m, 2H), 2.64-2.75 (m, 2H). $^{13}$C NMR (400 MHz, DMSO-d6) δ 183.55, 170.85, 149.23, 142.86, 138.78, 131.78, 129.29, 128.41, 128.33, 126.24, 125.05, 124.29, 112.57, 103.06, 65.78, 47.31, 33.33, 30.60

Example 26

Further characterization of DPX-4-0001 (ALE 408)

We have coupled 4-(hydroxyethyl)-N,N-dimethylaniline (IPU I) to ketorolac in the form of an ester prodrug (DPX-4-0001) (FIG. 3). The pK$_a$ value of IPU 1 (and thus DPX-4-0001) is about 5.2. At pH 2.02, the solubility of the hydrochloride salt of DPX-4-0001 is 65 µg/ml. At pH 7.4, the solubility decreases 1300-fold to about 0.05 µg/ml (neutral form). This should be noted that, according to Eq.

1, a similar relative solubility enhancement can be obtained at pH 4 in case an IPU with a p$K_a$ value of 7.2 was selected.

$$S_t = S_0 * (1 + 10^{pKa-pH}) \tag{Eq. 1}$$

In the following HPLC method used, the retention time of DPX-4-0001 and ketorolac were 4.5 and 6.5 min, respectively: Merck-Hitachi L-6200 pump connected to a Merck-Hitachi L-4000 UV detector and a Merck-Hitachi L-7200 autosampler (VWR International, Tokyo, Japan). Reversed phase chromatography was performed using a C18 Gemini® RP column (150×4.6 mm, 5 μm particles) (Phenomenex, Torrance, Calif., USA) equipped with a SecurityGuard precolumn (Phenomenex, Torrance, Calif., USA) with the column oven set at 30° C. The flow rate was set at 1 mL/min and the column effluent was monitored at 320 nm. The mobile phase consisted of 57.5% (v/v) methanol and 43.5% (v/v) of 0.1% (v/v) phosphoric acid.

Example 27

Dissolution of Prodrug in Synovial Fluid Followed by Formation of the Active Agent The stability of a suspension of DPX-4-0001 in 80% human synovial fluid pH 7.4 (SF) from arthritis patients was investigated at 37° C. The reaction was initiated by adding 5 ml preheated SF to 2 mg DPX-4-0001. At appropriate time intervals, 400 μl samples were taken and centrifuged for 5 min at 13.000 rpm and 200 μl of the supernatant was deproteinised with 400 μl acetonitrile. After centrifugation for 4 min at 13000 rpm, the supernatant was analysed by HPLC for DPX-4-0001 as well as formed ketorolac. The HPLC method described in Example 26 was applied.

As appears from FIG. 2, the concentration of dissolved DPX-4-0001 in SF increased during the first 3 hours of the experiment however remained low (about $2.2 \times 10^{-5}$ M) after 21 hours. The concentration of formed ketorolac in SF increased over time and after 21 hours 0.28 mM was found corresponding to conversion of 28% of the added amount of DPX-4-0001. The increased solubility of QPX-4-0001 in the synovial fluid (compared to buffer pH 7.4) can most likely be ascribed to binding of the prodrug to proteins residing in the synovial fluid. By extrapolation of the presented data, the total drug dose will be release over approximately 4 days.

For comparison, the stability of a suspension of DPX-4-0001 in 67 mM phosphate buffer pH 7.4 was investigated by the same procedure at 37° C. In this experiment, no significant degradation of DPX-4-0001 (to ketorolac) was observed and the final DPX-4-0001 concentration amounted to about $8 \times 10^{-7}$ M. The performed experiments strongly indicate that an esterase (currently not identified) present in the synovial fluid is responsible for the generation of ketorolac. Since the synovial disappearance half-lives of small-molecule drugs are in the range 2-5 h, the concentration of the active agent in the joint space is determined by the prodrug properties (i) solubility, (ii) degree of protein binding, and (iii) rate of cleavage of the prodrug bond, as well as (iv) the administered dose.

The obtained data for DPX-4-0001 gives indication that the prodrug ketorolac-IPU provides the expected prolongation of NSAID release (up to about 4 days) and prodrug cleavage requires and is effectively accomplished by the action of esterases (or other hydrolases) residing in the synovial fluid.

Example 28

Preliminary Precipitation Experiment No Esterases Present

A concentrated solution of DPX-4-0001 in 0.01 M HCl was prepared by adding 0.2 ml of $1 \times 10^{-5}$ M methanol solution of DPX-4-0001 to 1.0 ml 0.01 M HCl resulting in a final concentration of $1.7 \times 10^{-4}$ M. After addition of 300 μl of this solution (0.02 mg) to 5 ml 67 mM phosphate buffer pH 7.4, a precipitation process was observed. At appropriate time intervals, samples were withdrawn and centrifuged for 5 min at 13,000 rpm and the supernatant was analysed by HPLC for DPX-4-0001 and formed ketorolac. The HPLC method described in Example 26 was applied. After the initial precipitation phase, a low and fairly constant concentration of dissolved QPX-4-0001 over 25 h is observed. A slight increase in the ketorolac concentration is the result of pH dependent hydrolysis of the prodrug bond (FIG. 3).

Example 29

Solubility of DPX-2-0007 (JBX018) at pH 3.4 and Precipitation in Buffer pH 7.4

A suspension of DPX-2-0007 (as hydrochloride salt) was formed by adding 30 mg to 4 mL demineralized water. After rotation of the suspension at 37° C. for 3 days, 1.0 mL sample was taken and after filtration (disposable syringe filters), the solution was diluted in methanol:water 1:1 and analyzed immediately by HPLC for prodrug. Quantitation of DPX-2-0007 was done from peak area measurements in relations to those of standards analysed by HPLC at the same conditions. The pH in the solution was measured to 3.40. The following HPLC method was used: Merck Hitachi L 6200 pump connected to Merck Hitachi 4250 UV detector. Reversed phase chromatography was performed using a RP 18 Symmetry Shields® column (150×4.6 mm, 5 μm particles) equipped with a SecurityGuard precolumn (Phenomenex, Torrance, Calif., USA). The flow rate was set at 1 mL/min and the column effluent was monitored at 230 nm. The mobile phase consisted of 35% (v/v) acetonitrile and 65% (v/v) of 0.1% (v/v) phosphoric acid pH 3.2. The retention time of naproxen and DPX-2-0007 were 19 and 5.8 min, respectively.

The solubility of DPX-2-0007 at pH 3.4 was determined to 6.8+0.6 mg/mL. Thus, a 1000-fold increase in the solubility compared to the solubility of DPX-2-0007 in buffer pH 7.4 (PBS—see Table 1).

TABLE 1

Solubilities of the prodrugs ($S_{prodrug}$) in PBS (67 mM phosphate buffer pH 7.4), the apparent pseudo-zero-order rate constant ($k_0$) and the estimated pseudo first-order rate constant ($k_{hyd}$) for cleavage of the prodrugs in PBS and half-lives ($t_{1/2}$) for hydrolysis of the prodrugs in 80% human plasma at 37° C.

| Prodrug | $S_{prodrug} \pm SD$ µg/mL | mM | $k_0$ M/day | $k_{hyd}$ day$^{-1}$ | $t_{1/2\ in\ PBS}$ day | $t_{1/2\ in\ plasma}$ min |
|---|---|---|---|---|---|---|
| DPX-1-0001 | 0.01 | $2 \times 10^{-5}$ | | | | |
| DPX-1-0002 | <0.1 | <0.0002 | | | | |
| DPX-1-0004 | 3 ± 1 | 0.007 ± 0.001 | $1.1 \times 10^{-6}$ | $1.5 \times 10^{-1}$ | 5 | 25 |
| DPX-1-0005 | 1 | 0.003 | | | | |
| DPX-1-0006 | 7 ± 2 | 0.015 ± 0.004 | $2.4 \times 10^{-6}$ | $1.7 \times 10^{-1}$ | 4 | 3 |
| DPX-1-0007 | 43 ± 2 | 0.086 ± 0.003 | $2.5 \times 10^{-7}$ | $2.9 \times 10^{-3}$ | 242 | 49 |
| DPX-1-0008 | 0.3 | 0.0007 | | | | |
| DPX-1-0009 | <0.3 | <0.0007 | | | | |
| DPX-1-0010 | <0.4 | <0.0008 | | | | |
| DPX-1-0011 | 0.1 | 0.0002 | | | | |
| DPX-1-0012 | <0.3 | <0.0006 | | | | |
| DPX-2-0001 | <0.3 | <0.0008 | | | | |
| DPX-2-0002 | <0.2 | <0.0006 | | | | |
| DPX-2-0003 | <1 | <0.003 | | | | |
| DPX-2-0004 | 19 ± 1 | 0.052 ± 0.002 | $1.7 \times 10^{-6}$ | $3.3 \times 10^{-2}$ | 21 | 287 |
| DPX-2-0005 | 146 ± 5 | 0.45 ± 0.02 | | | | 64 |
| DPX-2-0006 | 5 ± 1 | 0.015 ± 0.002 | $1.0 \times 10^{-6}$ | $6.6 \times 10^{-2}$ | 11 | 511 |
| DPX-2-0007 | 7 ± 1 | 0.016 ± 0.001 | $1.0 \times 10^{-6}$ | $6.5 \times 10^{-2}$ | 11 | 62 |
| DPX-3-0004 | 15 ± 2 | 0.044 ± 0.004 | $1.0 \times 10^{-6}$ | $2.2 \times 10^{-2}$ | 32 | 755 |
| DPX-3-0006 | 4 ± 0.2 | 0.012 ± 0.001 | $5.7 \times 10^{-7}$ | $4.8 \times 10^{-2}$ | 15 | stable |
| DPX-3-0007 | 1 | 0.002 | | | | |
| DPX-4-0001 | 0.05 ± 0.03 | 0.0001 ± 0.0001 | | | Stable for 25 h | |

Upon addition of 1.0 mL of the concentrated aqueous solution of DPX-2-0007 at pH 3.4 to 1.0 mL 67 mM phosphate buffer pH 7.4, a precipitation was immediately observed. The pH in the suspension was measured to 7.0.

Example 30

Solubility of DPX-2-0006 at pH 3 in the Presence of N,N-Dimethyl Acetamide (DMA)

A suspension of DPX-2-0006 was formed by adding 10 mg to 3 mL demineralized water, 0.05 mL 0.100 M HCl was added to obtain a pH of 3. After rotation of the suspension at 37° C. for 1 days, 0.5 mL sample was taken and after filtration (disposable syringe filters), the solution was diluted in methanol:water 1:1 and analyzed immediately by HPLC for prodrug. Quantitation of DPX-2-0006 was done from peak area measurements in relations to those of standards analysed by HPLC at the same conditions. The HPLC method described in Example 29 was applied and the retention time of DPX-2-0006 was 14 min, respectively. N,N-dimethylacetamide (DMA) was added stepwise to the acidic suspension of DPX-2-0006 and the amount of DPX-2-000 dissolved in the presence of various volumes of DMA was determined after 1-3 days rotation at 37° C. as described above.

The solubility of DPX-2-0006 at pH 2.9 was 0.18 mg/ml. In the presence of 5%, 15%, 30% and 50% (v/v) DMA, the solubility was increased to 0.25, 0.35, 0.57 and 2.25 mg/ml, respectively.

Example 31

Determination of Solublities and Stabilities of the Prodrugs in Buffer pH 7.4

Suspensions of the prodrugs in 67 mM phosphate buffer pH 7.4 (PBS) were prepared by adding 10 mL PBS to approximately 5 mg prodrug. The suspensions were kept unstirred at 37° C. in an incubator hood. At appropriate time intervals over 23 days, about 500 µL samples were taken and after filtration (disposable syringe filters), the solutions were analyzed immediately by HPLC for parent drug and remaining prodrug. Quantitation of parent drug and prodrug was done from peak area measurements in relations to those of standards analysed by HPLC at the same conditions. For the naproxen prodrug, the HPLC method described in example 29 were applied. For the diclofenac and ibuprofen prodrugs, the following method was used: Merck Hitachi L 6000 pump connected to Merck Hitachi 4250 UV detector. Reversed phase chromatography was performed using a C18 Gemini® RP column (150×4.6 mm, 5 µm particles) (Phenomenex, Torrance, Calif., USA) equipped with a SecurityGuard pre-column (Phenomenex, Torrance, Calif., USA). The flow rate was set at 1 mL/min and the column effluent was monitored at 230 nm. The mobile phase consisted of 35% (v/v) acetonitrile and 65% (v/v) of 0.1% (v/v) phosphoric acid pH 3.2. The retention times varied in the range of 3 to 30 min.

From the observed relatively stable concentration of dissolved prodrugs measured in the suspensions after 8-9 day up to 23 days, the solubilities of the prodrugs ($S_{prodrug}$) were determined. In this time interval, the rate of appearance of parent drug was determined and an apparent pseudo-zero-order rate constant ($k_0$) was obtained. By assuming that the dissolution rates were much faster than the conversion of the prodrugs to the parent drug, pseudo first-order rate constants ($k_{hyd}$) for cleavage of the prodrugs were calculated according to:

$$-\frac{d[\text{Prodrug}]}{dt} = \frac{d[\text{Drug}]}{dt} = k_{hyd} = S_{prodrug} = k_0$$

All data are summarized in Table 1.

Example 32

Hydrolysis of the Prodrugs in 80% Human Plasma

At 37±0.5° C., the hydrolysis rate of the prodrugs was measured in 80% human plasma. An appropriate aliquot (20-100 μL) of 1 mg/ml prodrug solution in methanol was transferred to 5.0 ml of preheated plasma. At appropriate time intervals, 300 μl sample aliquots were withdrawn and transferred to 600 μl acetonitrile and mixed thoroughly. After centrifugation at 13500 rpm for 5 min, the supernatant was analyzed by HPLC for parent drug and remaining prodrug. The HPLC methods described in Example 29 and 31 were applied.

The half-lives for cleavage of the prodrugs in 80% human plasma were in the range 3-755 min (DPX-3-0006 remained intact after incubation in plasma for 10 h).

REFERENCES

Ref. 1: Reuben et al.
Reuben S. S., Connelly N. R. (1995) Postoperative analgesia for outpatient arthroscopic knee surgery with intraarticular bupivacaine and ketorolac. Anesth Analg 80: 1154-1157

Ref. 2: Rasmussen et al.
Rasmussen S., Larsen A. S., Thomsen S. T., Kehlet H. (1998) Intra-articular glucocorticoid, bupivacaine and morphine reduces pain, inflammatory response and convalescence after arthroscopic meniscectomy. Pain 78: 131-134

Ref. 3: R. Williams
pKa Data Compiled by R. Williams (downloadable from http://research.chem.opu.edu/brpgroup/pKa_compilation.pdf)

Ref. 4: Caballero et al.
Caballero et al. (2006) "Theoretical prediction of relative and absolute pKa values of aminopyridines", Biophysical Chemistry 124(2), p 155-160 (Ref. 3).

Ref. 5: Drustrup et al.
Drustrup et al. (1991) "Utilization of prodrugs to enhance the transdermal absorption of morphine", International Journal of Pharmaceutics 71, 105-116

Specific embodiments include the following items

1. A compound of formula (I):

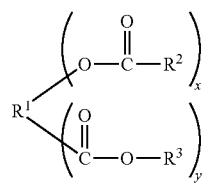

(I)

wherein:
$R^1$ represents an immobility promoting unit selected from an organic moiety with a molecular weight lower than 1000 g/mol comprising one or more nitrogen containing moieties each with a $pK_a$ of between 4 and 7.4 at 37° C.;
—O—(C=O)—$R^2$ represents a acyloxy residue of a carboxylic acid group containing active pharmaceutical ingredient, preferably a non-steroidal anti-inflammatory agent or immunosuppressant;
—O—$R^3$ represents a hydroxyl residue of a hydroxyl group containing active pharmaceutical agent, preferably an opiate or a corticosteroid;
x is an integer selected from 0, 1, 2, 3 or 4;
y is an integer selected from 0, 1, 2, 3 or 4;
where the sum x+y is at least 1;
and pharmaceutically acceptable salts, solvates and hydrates thereof.

2. Compound according to item 1, wherein x is 1, 2, 3, or 4, and y is 0 or wherein x is 0, and y is 1, 2, 3, or 4.

3. Compound according to item 1, wherein x is 0, and y is 1, or wherein x is 1, and y is 0.

4. Compound according to item 1, having a solubility of between 0.01 μM and 1 μM in 10 mM PBS at 37° C. and pH 7.4, and a solubility of more than 100 μM at pH 3.

5. Compound according to item 1, wherein the one or more nitrogen containing moieties are selected from substituted or unsubstituted phenylamino, imidazolyl, isoquinolinyl, quinolinyl, benzimidazolyl, acridinyl.

6. Compound according to item 1, wherein the carboxylic acid group containing active pharmaceutical ingredient is selected from the list consisting of: naproxen, ibuprofen, ketorolac, ketoprofen, fenoprofen, flurbiprofen, oxaprofen, diclofenac, tolmetin, tolfenamic acid, mefenamic acid, sulindac, indomethacin, salicylic acid, acetylsalicylic acid, deflunisal, loxoprofen, indoprofen, priprofen, clidanac, fenclorac, meclofenamate, benoxaprofen, carprofen, isofezolac, acedofenac, fenbufen, etodolic acid, fleclozic acid, amfenac, efenamic adic, bromfenac, flenclofenac, alcofenac, orpanoxin, zomopirac, flufenamic acid, niflumic acid, pranoprofen, zaltoprofen, and suprofen.

7. Compound according to item 1, wherein the hydroxyl group containing active pharmaceutical ingredient is selected from the list consisting of: prednisolone, methylprednisolone, triamcinolone and dexamethasone.

8. Compound according to item 1, wherein the hydroxyl group containing active pharmaceutical agent is selected from the list consisting of: codeine, morphine, oripavine, dihydrocodeine, hydromorphone, oxycodone, oxymorphone, ohmefentanyl, ketobemidone, dezocine, pentazocine, phenazocine, buprenorphine, dihydroetorphine, etorphine, butorphanol, nalbuphine, levorphanol, meptazinol, tramadol, tapentadol.

9. Compound according to item 1, wherein $R^1$ is selected from the list consisting of the $R^1$ moieties of the $R^1$—OH and $R^1$—COOH compounds below:

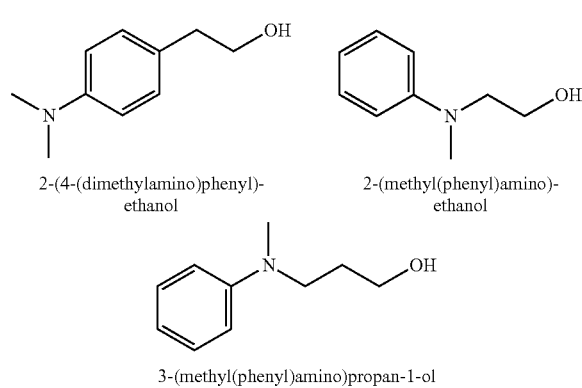

2-(4-(dimethylamino)phenyl)-ethanol 2-(methyl(phenyl)amino)-ethanol 3-(methyl(phenyl)amino)propan-1-ol -continued

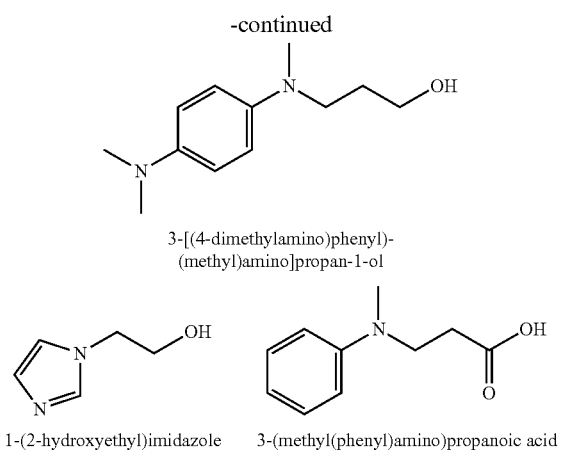

3-[(4-dimethylamino)phenyl)-
(methyl)amino]propan-1-ol

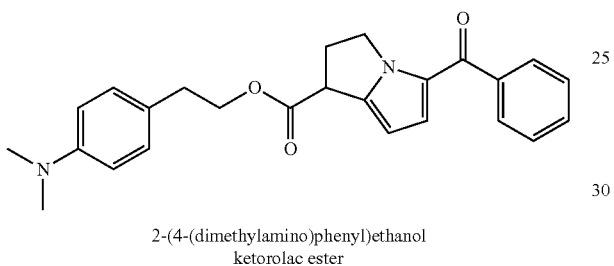

1-(2-hydroxyethyl)imidazole     3-(methyl(phenyl)amino)propanoic acid

10. Compounds of formula I, selected from the list consisting of:

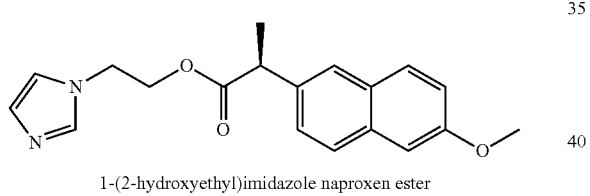

2-(4-(dimethylamino)phenyl)ethanol
ketorolac ester

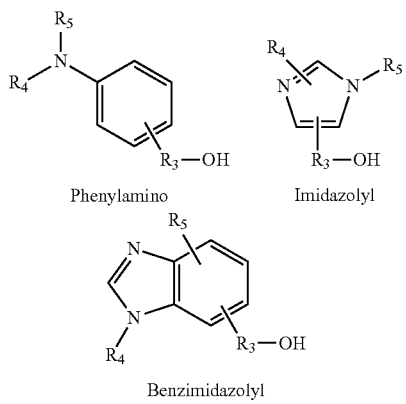

1-(2-hydroxyethyl)imidazole naproxen ester

11. Pharmaceutical composition, characterised in that it contains a therapeutically effective amount of a compound according to any one of claims 1 to 10, and at least one pharmaceutically acceptable carrier, vehicle and/or adjuvant.

12. Pharmaceutical composition according to item 11, wherein the composition is suitable for intra-articular injection.

13. Compound or pharmaceutical composition according to any one of items 1-12 for use as a medicament.

14. Compound or pharmaceutical composition according to any one of items 1-12 for use in treatment of inflammation in joints.

15. Compound or pharmaceutical composition according to any one of items 1-12 for use in treatment of postoperative pain control following arthroscopic surgery.

16. A method for the preparation of a medicament with anti-inflammatory activity, characterized in that it comprise a prodrug according to any one of items 1-12 as an active ingredient.

The invention claimed is:

1. A compound of formula (I):

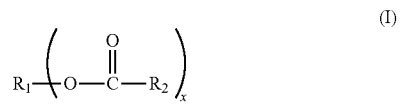

wherein:

$R_1$ represents an immobility promoting unit (IPU) with a molecular weight lower than 1000 g/mol and a $pK_a$ of between 4 and 7.6 at 37° C., wherein the IPU is selected from the group consisting of:

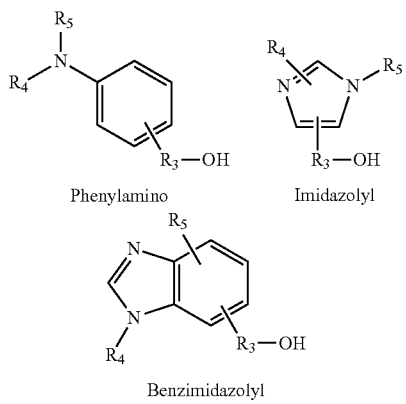

Phenylamino     Imidazolyl

Benzimidazolyl wherein $R_3$ is attached on any ring carbon or any nitrogen of the IPU and $R_3$ is straight or branched $C_{1-8}$ alkyl or alkoxyalkyl, with the proviso that when $R_3$ is attached on a nitrogen atom $R_3$ is not —$CH_2$—

$R_4$ and $R_5$ are each independently hydrogen, straight or branched $C_{1-8}$ alkyl, alkoxyalkyl or phenyl, or when $R_1$ is a phenylamino or benzimidazolyl moiety as set forth above, $R_4$ may be $R_3$, or when $R_1$ is an imidazolyl moiety as set forth above, $R_5$ may be $R_3$;

—O—(C=O)—$R_2$ represents an acyloxy residue of a carboxylic acid group of;

and x is 1;

salts, solvates or hydrates thereof, wherein the aqueous solubility of the compound is pH dependent, such that the aqueous solubility at a pH between 2 to 6 pH units lower than a pH of a physiological fluid having a pH of from 6 to 8 is at least 100 times higher than its aqueous solubility at the pH of the physiological fluid.

2. A compound according to claim 1, wherein $R_1$ is selected from the group consisting of the $R_1$ moieties of the following $R_1$—OH compounds:

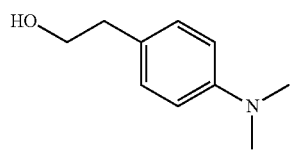

2-(4-(dimethylamino)phenyl)ethanol

-continued

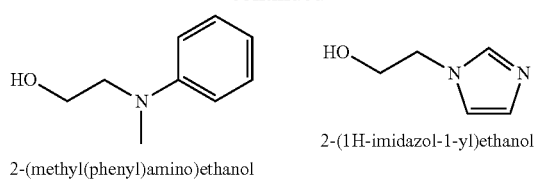

2-(methyl(phenyl)amino)ethanol 2-(1H-imidazol-1-yl)ethanol

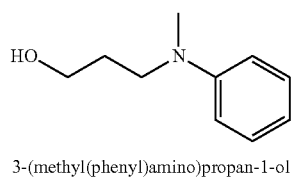

3-(methyl(phenyl)amino)propan-1-ol

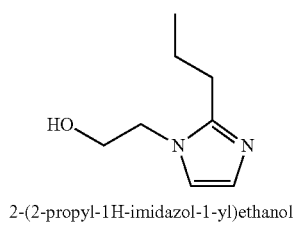

2-(2-propyl-1H-imidazol-1-yl)ethanol

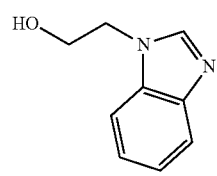

2-(1H-benzo[d]imidazol-1-yl)ethanol

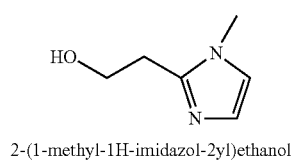

2-(1-methyl-1H-imidazol-2yl)ethanol

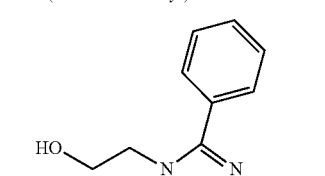

6-(1H-imidazol-1-yl)hexan-1-ol

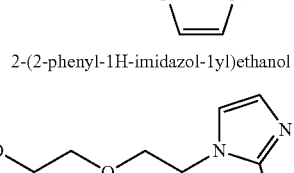

2-(2-phenyl-1H-imidazol-1yl)ethanol

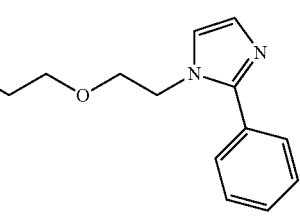

2-(2-(2-phenyl-1H-imidazol-1-yl)ethoxy)ethanol

-continued

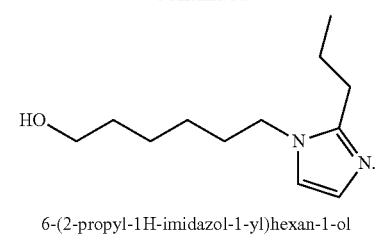

6-(2-propyl-1H-imidazol-1-yl)hexan-1-ol

3. A compound according to claim 1, selected from the group consisting of:

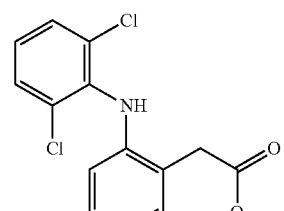

DPX-1-0001

(ALE 463, JBX028)

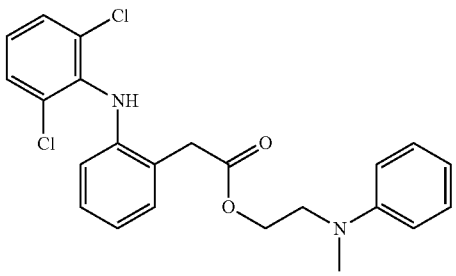

DPX-1-0002

(ALE 482, JBX027)

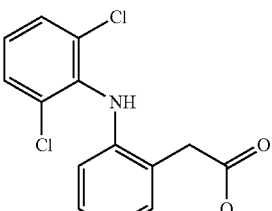

DPX-1-0005

(ALE 460, JBX026)

-continued

DPX-1-0006

(JBX022)

DPX-1-0007

(sdnX-18)

DPX-1-0008

(ALE 459-3)

DPX-1-0009

-continued

DPX-1-0010

DPX-1-0011

DPX-1-0012

4. A pharmaceutical composition comprising a therapeutically effective amount of a compound according to claim 1, and at least one pharmaceutically acceptable carrier, vehicle and/or adjuvant.

5. A pharmaceutical composition according to claim 4, wherein the composition is suitable for intra-articular injection.

6. A method of treating postoperative pain and/or inflammation in a patient in need thereof, comprising administering a therapeutically effective amount of a compound according to claim 1 to the patient.

7. A method of treating postoperative pain following arthroscopic surgery in a patient in need thereof, comprising administering a therapeutically effective amount of a compound according to claim 1 to the patient.

8. A composition for intra-articular injection comprising a compound according to claim 1, wherein the composition is in the form of an aqueous solution having a pH of from 1.5 to 5, from which the compound of formula I precipitates in the joint of a patient, at least partly, after administration.

9. A composition according to claim 8, wherein $R_1$ is selected from the group consisting of the $R_1$ moieties of the following $R_1$—OH compounds:

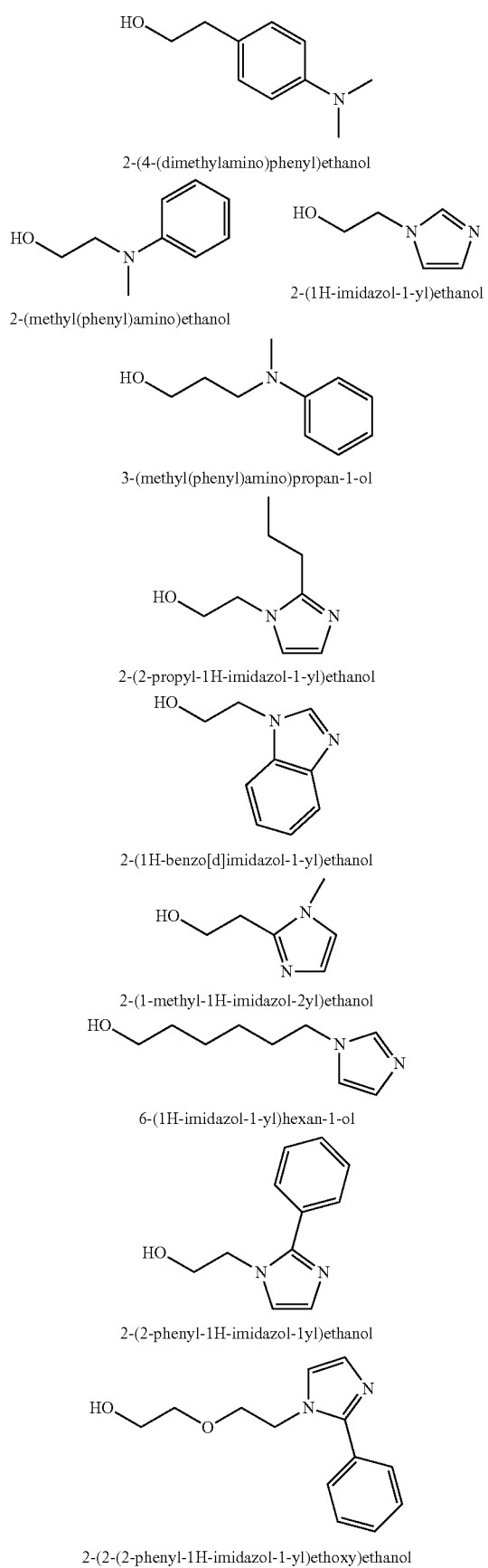
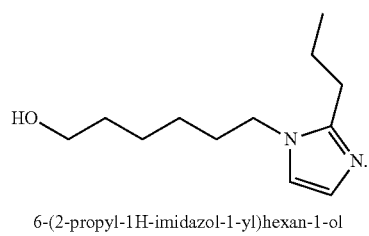
6-(2-propyl-1H-imidazol-1-yl)hexan-1-ol
10. A composition according to claim 8, wherein the compound is selected from the group consisting of:
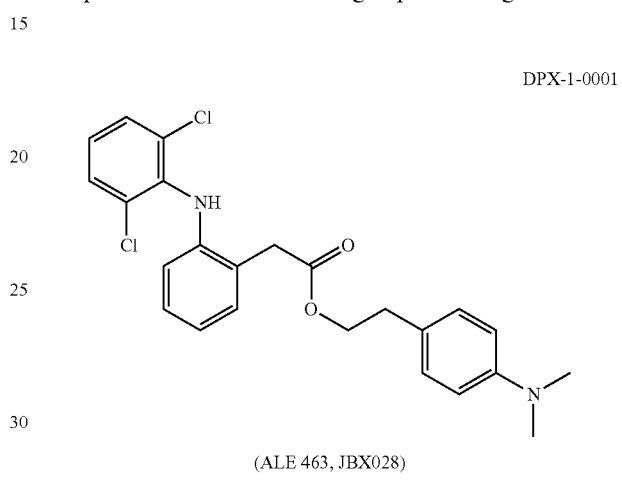
(ALE 463, JBX028)
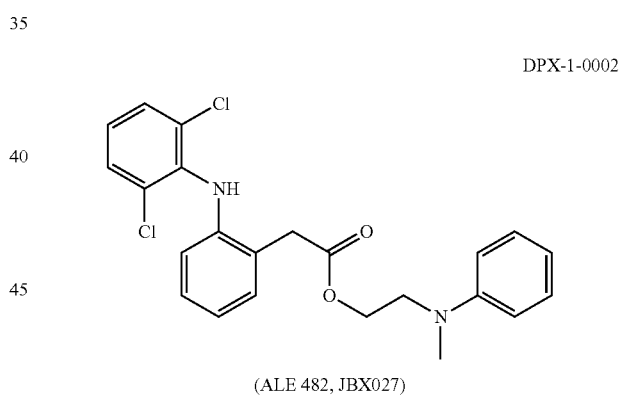
(ALE 482, JBX027)
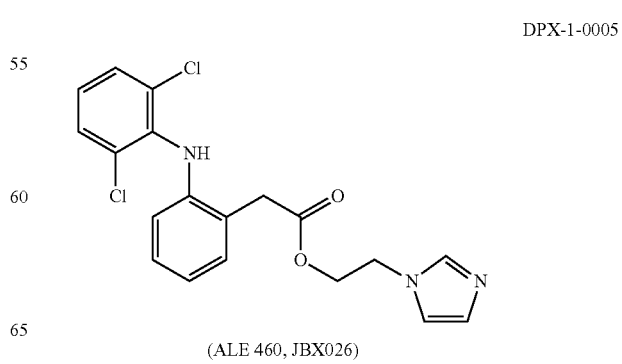
(ALE 460, JBX026)

-continued

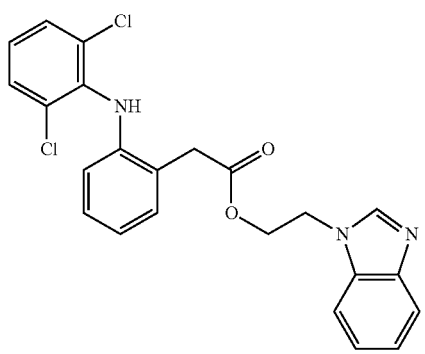

(JBX022) DPX-1-0006

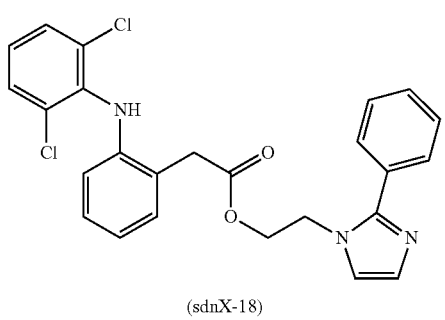

(sdnX-18) DPX-1-0007

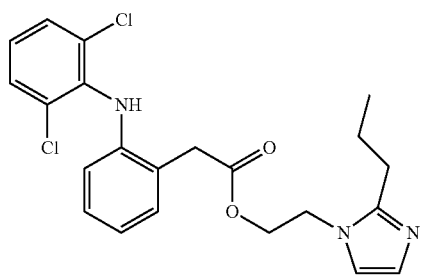

(ALE 459-3) DPX-1-0008

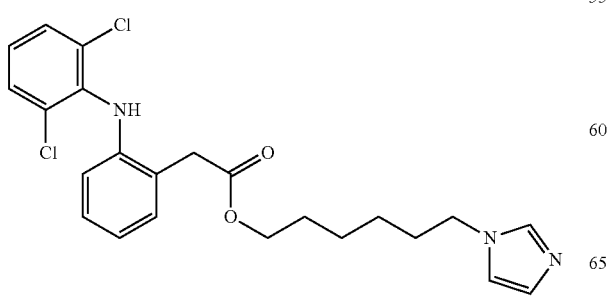

DPX-1-0009

-continued

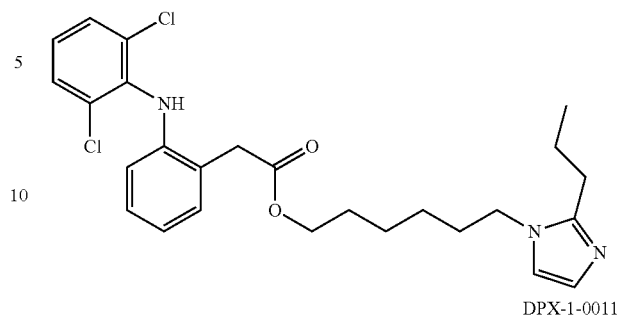

DPX-1-0010

DPX-1-0011

DPX-1-0012

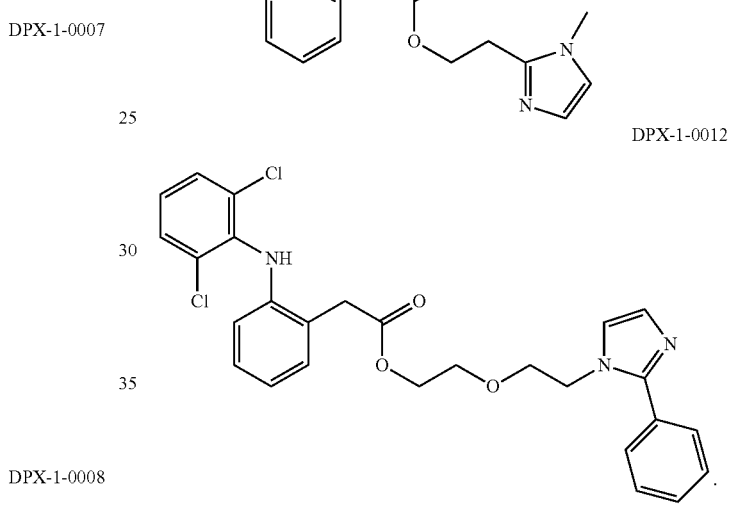

11. A method of treating postoperative pain and/or inflammation in a patient in need thereof, comprising administering a therapeutically effective amount of a composition according to claim 8 to the patient.

12. A method of treating postoperative pain and/or inflammation following arthroscopic surgery in a patient in need thereof, comprising administering a therapeutically effective amount of a composition according to claim 8 to the patient.

13. A compound of formula:

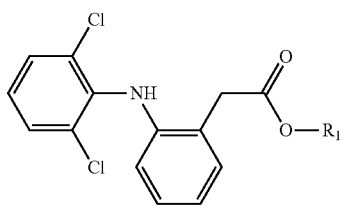

wherein:

$R_1$ represents an immobility promoting unit (IPU) with a molecular weight lower than 1000 g/mol and a $pK_a$ of between 4 and 7.6 at 37° C., wherein the IPU is selected from the group consisting of:

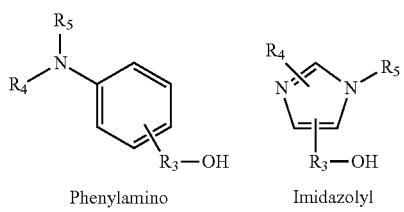

Phenylamino     Imidazolyl

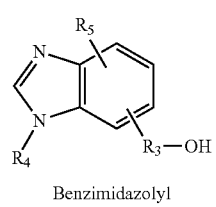

Benzimidazolyl wherein $R_3$ is attached on any ring carbon or any nitrogen of the IPU and $R_3$ is straight or branched $C_{1-8}$ alkyl or alkoxyalkyl, with the proviso that when $R_3$ is attached on a nitrogen atom $R_3$ is not —$CH_2$—, and $R_4$ and $R_5$ are each independently hydrogen, straight or branched $C_{1-8}$ alkyl, alkoxyalkyl or phenyl, or when $R_1$ is a phenylamino or benzimidazolyl moiety as set forth above, $R_4$ may be $R_3$, or when $R_1$ is an imidazolyl moiety as set forth above, $R_5$ may be $R_3$;

salts, solvates or hydrates thereof, wherein the aqueous solubility of the compound is pH dependent, such that the aqueous solubility at a pH between 2 to 6 pH units lower than a pH of a physiological fluid having a pH of from 6 to 8 is at least 100 times higher than its aqueous solubility at the pH of the physiological fluid.

14. A compound according to claim 13, wherein $R_1$ is selected from the group consisting of the $R_1$ moieties of the following $R_1$—OH compounds:

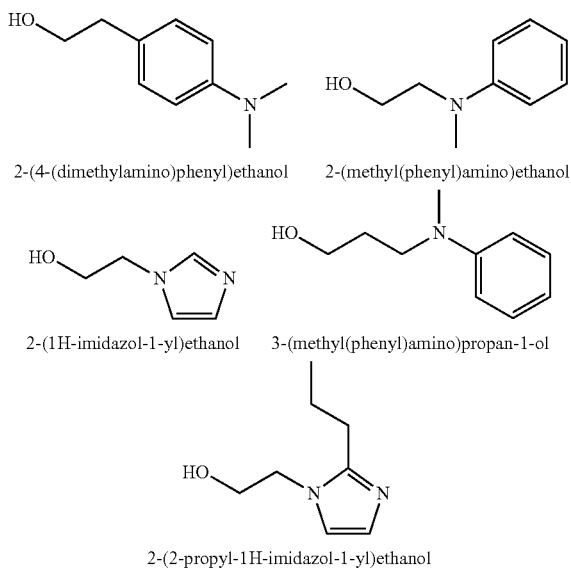

2-(4-(dimethylamino)phenyl)ethanol     2-(methyl(phenyl)amino)ethanol 2-(1H-imidazol-1-yl)ethanol     3-(methyl(phenyl)amino)propan-1-ol 2-(2-propyl-1H-imidazol-1-yl)ethanol -continued

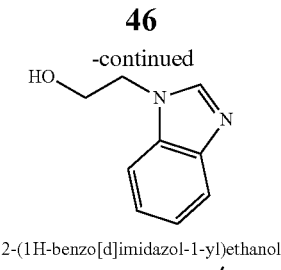

2-(1H-benzo[d]imidazol-1-yl)ethanol

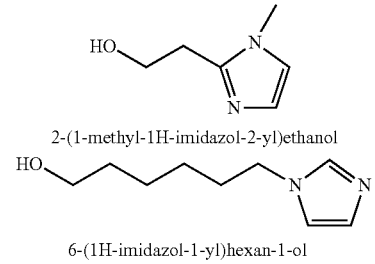

2-(1-methyl-1H-imidazol-2-yl)ethanol 6-(1H-imidazol-1-yl)hexan-1-ol

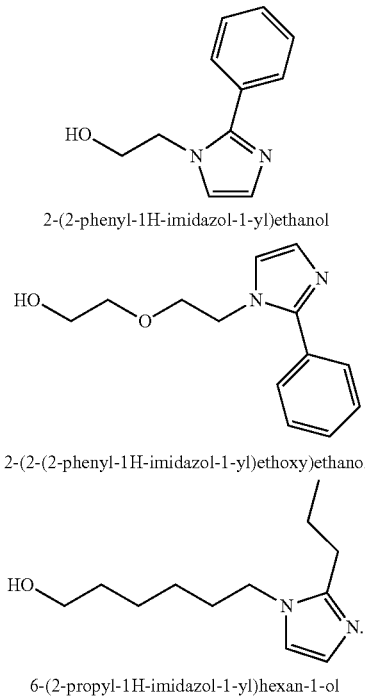

2-(2-phenyl-1H-imidazol-1-yl)ethanol 2-(2-(2-phenyl-1H-imidazol-1-yl)ethoxy)ethanol 6-(2-propyl-1H-imidazol-1-yl)hexan-1-ol 15. A pharmaceutical composition comprising a therapeutically effective amount of a compound according to claim 13, and at least one pharmaceutically acceptable carrier, vehicle and/or adjuvant.

16. A pharmaceutical composition according to claim 15, wherein the composition is suitable for intra-articular injection.

17. A method of treating postoperative pain and/or inflammation in a patient in need thereof, comprising administering a therapeutically effective amount of a compound according to claim 13 to the patient.

18. A method of treating postoperative pain following arthroscopic surgery in a patient in need thereof, comprising administering a therapeutically effective amount of a compound according to claim 13 to the patient.

19. A composition for intra-articular injection comprising a compound according to claim 13, wherein the composition is in the form of an aqueous solution having a pH of from 1.5 to 5, from which the compound of formula I precipitates in the joint of a patient, at least partly, after administration.

20. A composition for intra-articular injection comprising a compound according to claim 14, wherein the composition is in the form of an aqueous solution having a pH of from 1.5 to 5, from which the compound of formula I precipitates in the joint of a patient, at least partly, after administration.

* * * * *